US011375934B2

(12) United States Patent
Okada et al.

(10) Patent No.: US 11,375,934 B2
(45) Date of Patent: Jul. 5, 2022

(54) BIOMAGNETIC MEASUREMENT APPARATUS, BIOLOGICAL INFORMATION MEASUREMENT APPARATUS, AND BIOMAGNETIC MEASUREMENT METHOD

(71) Applicants: Yoshinori Okada, Kanagawa (JP); Yoshihisa Naijo, Kanagawa (JP); Hiroshi Deguchi, Kanagawa (JP); Taishi Watanabe, Tokyo (JP); Yuki Miyano, Kanagawa (JP); Shigenori Kawabata, Tokyo (JP)

(72) Inventors: Yoshinori Okada, Kanagawa (JP); Yoshihisa Naijo, Kanagawa (JP); Hiroshi Deguchi, Kanagawa (JP); Taishi Watanabe, Tokyo (JP); Yuki Miyano, Kanagawa (JP); Shigenori Kawabata, Tokyo (JP)

(73) Assignees: Ricoh Company, Ltd., Tokyo (JP); NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 428 days.

(21) Appl. No.: 16/198,962

(22) Filed: Nov. 23, 2018

(65) Prior Publication Data

US 2019/0167135 A1      Jun. 6, 2019

(30) Foreign Application Priority Data

Dec. 1, 2017   (JP) .............................. JP2017-231571
Oct. 31, 2018  (JP) .............................. JP2018-205986

(51) Int. Cl.
*A61B 5/00*       (2006.01)
*A61B 5/242*      (2021.01)
(Continued)

(52) U.S. Cl.
CPC .............. *A61B 5/242* (2021.01); *A61B 5/704* (2013.01); *A61B 6/032* (2013.01); *A61B 6/0407* (2013.01); *A61B 2562/0223* (2013.01)

(58) Field of Classification Search
CPC ......... A61B 5/242; A61B 5/704; A61B 6/032; A61B 6/0407; A61B 2562/0223
See application file for complete search history.

(56) References Cited

U.S. PATENT DOCUMENTS

| 4,996,479 A | 2/1991 | Hoenig |
| 6,628,978 B1 * | 9/2003 | Kondo .................. A61B 5/242 |
| | | 324/261 |

(Continued)

FOREIGN PATENT DOCUMENTS

| JP | H02-114941 | 4/1990 |
| JP | H05-154122 | 6/1993 |

(Continued)

OTHER PUBLICATIONS

Sumiya, S. et al., Magnetospinography visualizes electrophysiological activity in the cervical spinal cord, Scientific Reports, May 19, 2017, vol. 7, No. 1, 2192, pp. 1-12.

(Continued)

*Primary Examiner* — Joseph M Santos Rodriguez
*Assistant Examiner* — Adam D. Kolkin
(74) *Attorney, Agent, or Firm* — IPUSA, PLLC

(57) ABSTRACT

A biomagnetic measurement apparatus includes a table on which a subject is placed; a biomagnetic detector configured to detect a biomagnetic field of the subject; a supporter configured to support a detection target region from which the biomagnetic field of the subject is detected; a radiation detector provided below the supporter; and a position changer configured to change relative positions of the biomagnetic detector and the detection target region. The (Continued)

supporter has a surface shape that corresponds to a surface of the biomagnetic detector.

18 Claims, 19 Drawing Sheets

(51) Int. Cl.
*A61B 6/03* (2006.01)
*A61B 6/04* (2006.01)

(56) References Cited

U.S. PATENT DOCUMENTS

| | | | |
|---|---|---|---|
| 8,583,208 | B2 | 11/2013 | Adachi et al. |
| 2004/0133097 | A1* | 7/2004 | Bonutti ............... A61G 13/12 600/415 |
| 2009/0295385 | A1* | 12/2009 | Brazdeikis ........... A61B 5/0515 324/309 |
| 2015/0131775 | A1* | 5/2015 | Yorkston ............. A61B 6/4452 378/17 |
| 2016/0242724 | A1* | 8/2016 | Lavallee ............... G06T 7/0012 |
| 2018/0092561 | A1 | 4/2018 | Kawabata et al. |

FOREIGN PATENT DOCUMENTS

| | | | |
|---|---|---|---|
| JP | 3451190 | 9/2003 | |
| JP | 3454254 | 10/2003 | |
| JP | 3950629 | 8/2007 | |
| JP | 2009-172175 | 8/2009 | |
| JP | 4397276 | 1/2010 | |
| JP | 4834076 | 12/2011 | |
| JP | 2012-055514 | 3/2012 | |
| JP | 4952914 | 6/2012 | |
| JP | 5136084 | 2/2013 | |
| JP | 5137149 | 2/2013 | |
| JP | 2016-221184 | 12/2016 | |
| JP | 2018-057843 | 4/2018 | |
| WO | WO-2005089651 A1 * | 9/2005 | ............. A61B 6/032 |
| WO | 2007/099697 | 9/2007 | |
| WO | WO-2016175020 A1 * | 11/2016 | ......... A61B 5/04005 |
| WO | 2017/150207 | 9/2017 | |

OTHER PUBLICATIONS

Japanese Office Action for 2018-205986 dated Apr. 12, 2022.

* cited by examiner

FIG.12
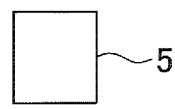
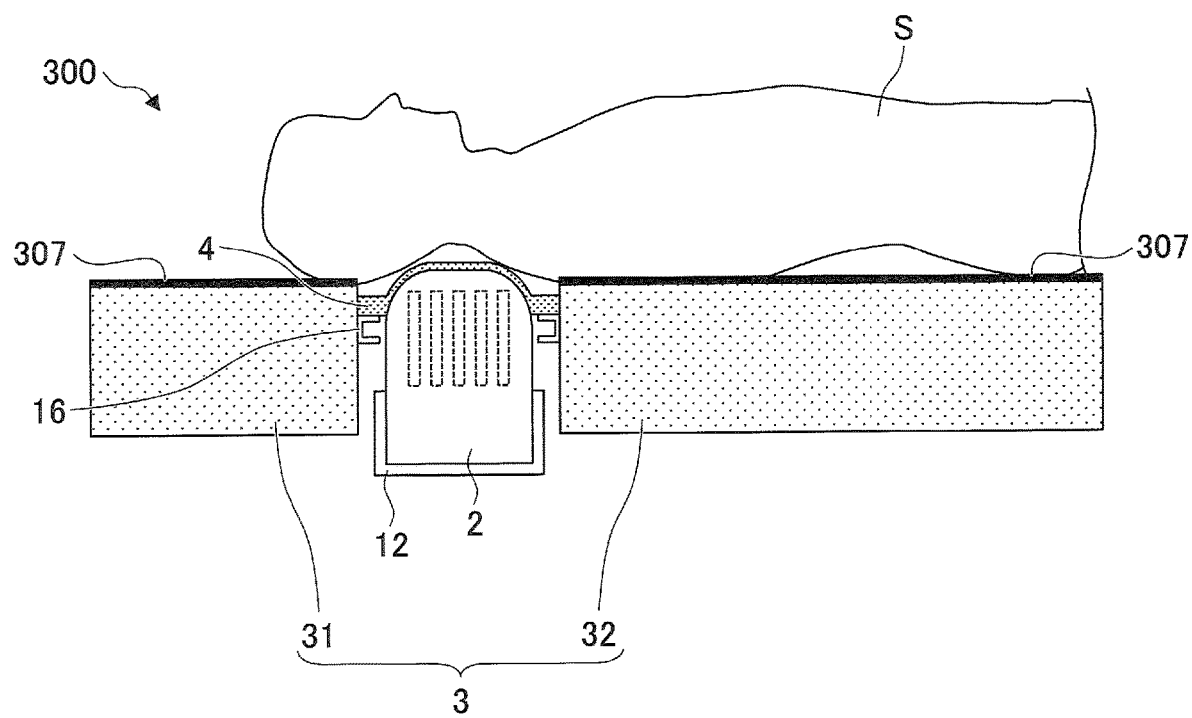

BIOMAGNETIC MEASUREMENT APPARATUS, BIOLOGICAL INFORMATION MEASUREMENT APPARATUS, AND BIOMAGNETIC MEASUREMENT METHOD

CROSS-REFERENCE TO RELATED APPLICATION

The present application is based on and claims priority under 35 U.S.C. § 119 to Japanese Patent Application No. 2017-231571, filed on Dec. 1, 2017 and Japanese Patent Application No. 2018-205986, filed on Oct. 31, 2018, the contents of which are incorporated herein by reference in their entirety.

BACKGROUND OF THE INVENTION

1. Field of the Invention

The present invention relates to a biomagnetic measurement apparatus, a biological information measurement apparatus, and a biomagnetic measurement method.

2. Description of the Related Art

A biomagnetic measurement apparatus for measuring a weak biomagnetic field generated from the heart, the spinal cord, and the peripheral nerves, etc., of a subject, has a function of detecting the biomagnetic field caused by a weak current caused by excitation of cells constituting these organs, and this is an important technique for the diagnosis of heart diseases and nerve diseases, etc. The information obtained from the biomagnetic measurement is superimposed on and displayed with a morphological image obtained by an image diagnostic apparatus. As the image diagnostic apparatus, a simple x-ray examination apparatus or a magnetic resonance imaging (MRI) diagnostic apparatus, etc., is used, and in general, the morphological image is photographed at a location different from where the biomagnetic measurement is performed.

Patent Document 1: Japanese Unexamined Patent Application Publication No. 2009-172175
Patent Document 2: Japanese Unexamined Patent Application Publication No. 2016-221184
Patent Document 3: WO 2017/150207
Patent Document 4: WO 2007/099697

SUMMARY OF THE INVENTION

An aspect of the present invention provides a biomagnetic measurement apparatus, a biological information measurement apparatus, and a biomagnetic measurement method, in which one or more of the disadvantages of the related art are reduced.

According to one aspect of the present invention, there is provided a biomagnetic measurement apparatus including a table on which a subject is placed; a biomagnetic detector configured to detect a biomagnetic field of the subject; a supporter configured to support a detection target region from which the biomagnetic field of the subject is detected; a radiation detector provided below the supporter; and a position changer configured to change relative positions of the biomagnetic detector and the detection target region, wherein the supporter has a surface shape that corresponds to a surface of the biomagnetic detector.

BRIEF DESCRIPTION OF THE DRAWINGS

FIG. 12 is a diagram (part 2) illustrating a configuration of a biomagnetic measurement apparatus according to the third embodiment of the present invention;

DETAILED DESCRIPTION OF THE PREFERRED EMBODIMENTS

In the related art, the subject moves between the image diagnostic apparatus and the biomagnetic measurement apparatus, and, therefore, it is extremely difficult to superimpose the respective measurement results with high precision. For example, when the subject moves between a radiation irradiation device and a biomagnetic measurement apparatus, the trunk (spine) of the subject is warped or bent down in the longitudinal direction or the lateral direction, or the joints of the four limbs of the subject are bent or extended. Therefore, it is extremely difficult to precisely match the position information of the subject obtained by the image diagnostic apparatus and the position of the subject at the time of examination with the biomagnetic measurement apparatus.

A problem to be solved by an embodiment of the present invention is to provide a biomagnetic measurement apparatus, a biological information measurement apparatus, and a biomagnetic measurement method by which the image diagnosis result and the biomagnetic measurement result can be easily superimposed with high precision.

Hereinafter, embodiments of the present invention will be described in detail; however, the present invention is not limited to the following embodiments, and may be implemented with appropriate modifications within the scope of the present invention.

First Embodiment

Figure 1:
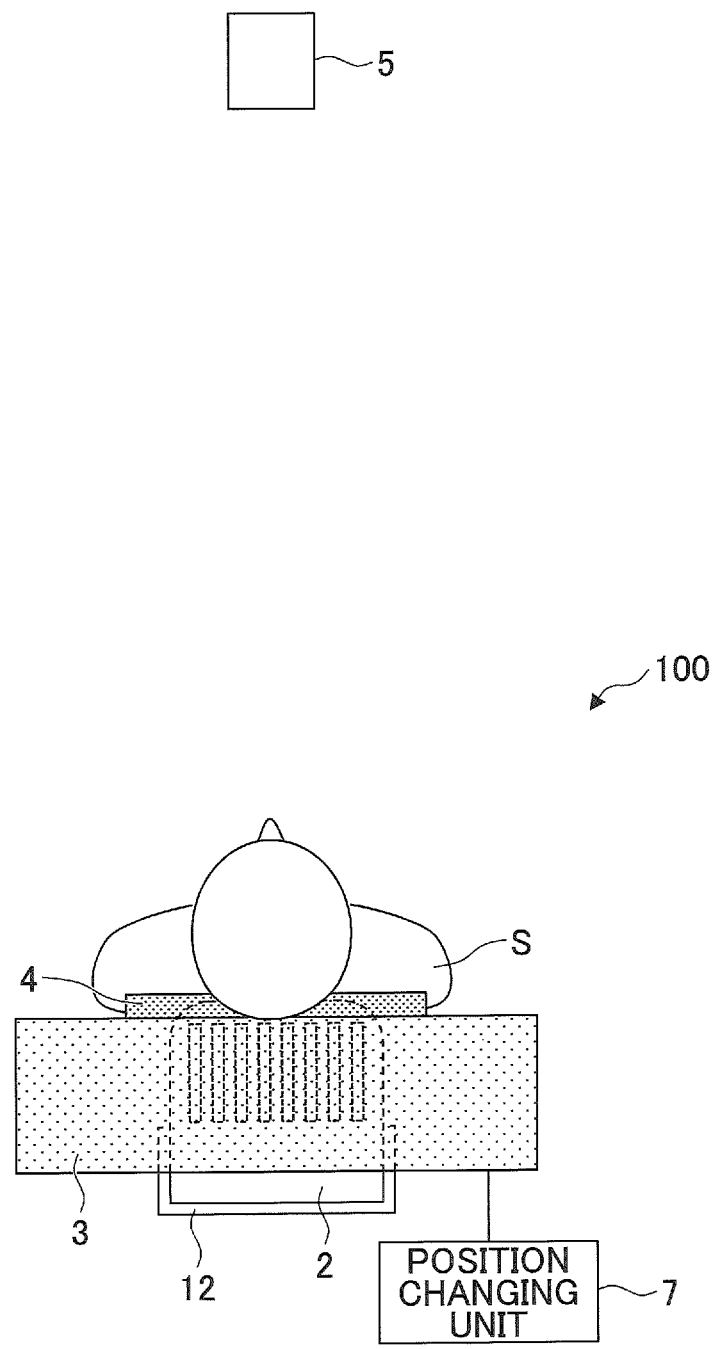
FIG. 1 is a diagram (part 1) illustrating a configuration of a biomagnetic measurement apparatus according to a first embodiment of the present invention.
Figure 2:
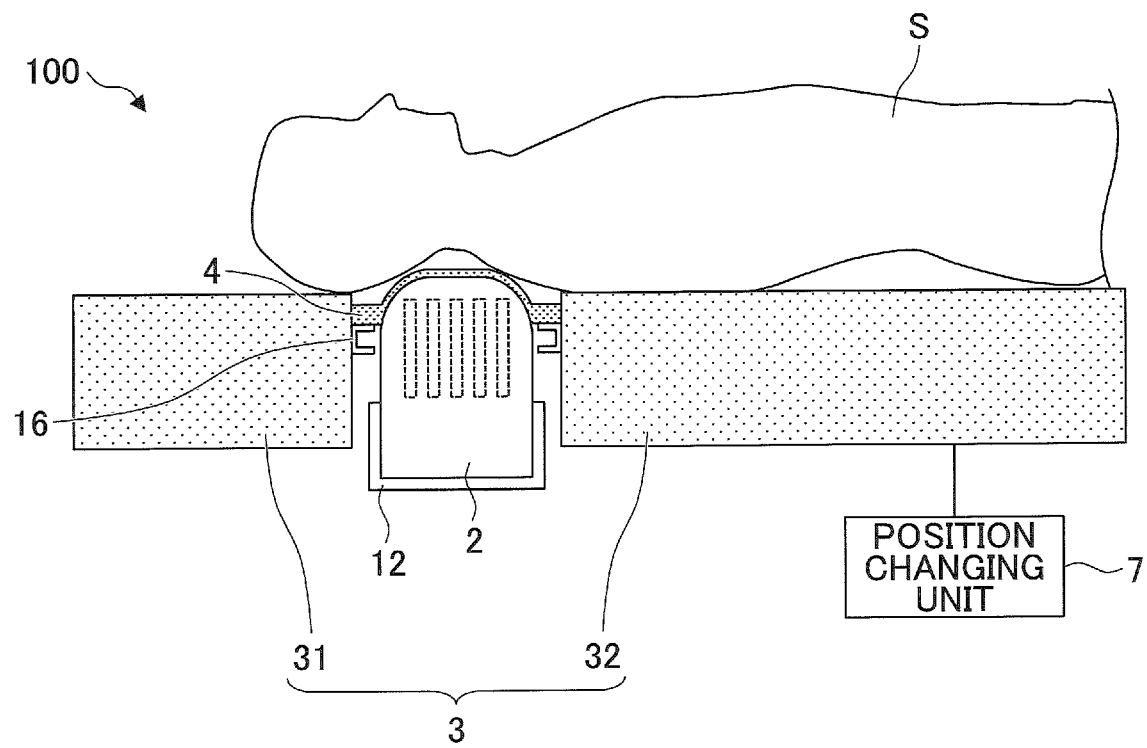
FIG. 2 is a diagram (part 2) illustrating a configuration of a biomagnetic measurement apparatus according to the first embodiment of the present invention.
Figure 3:
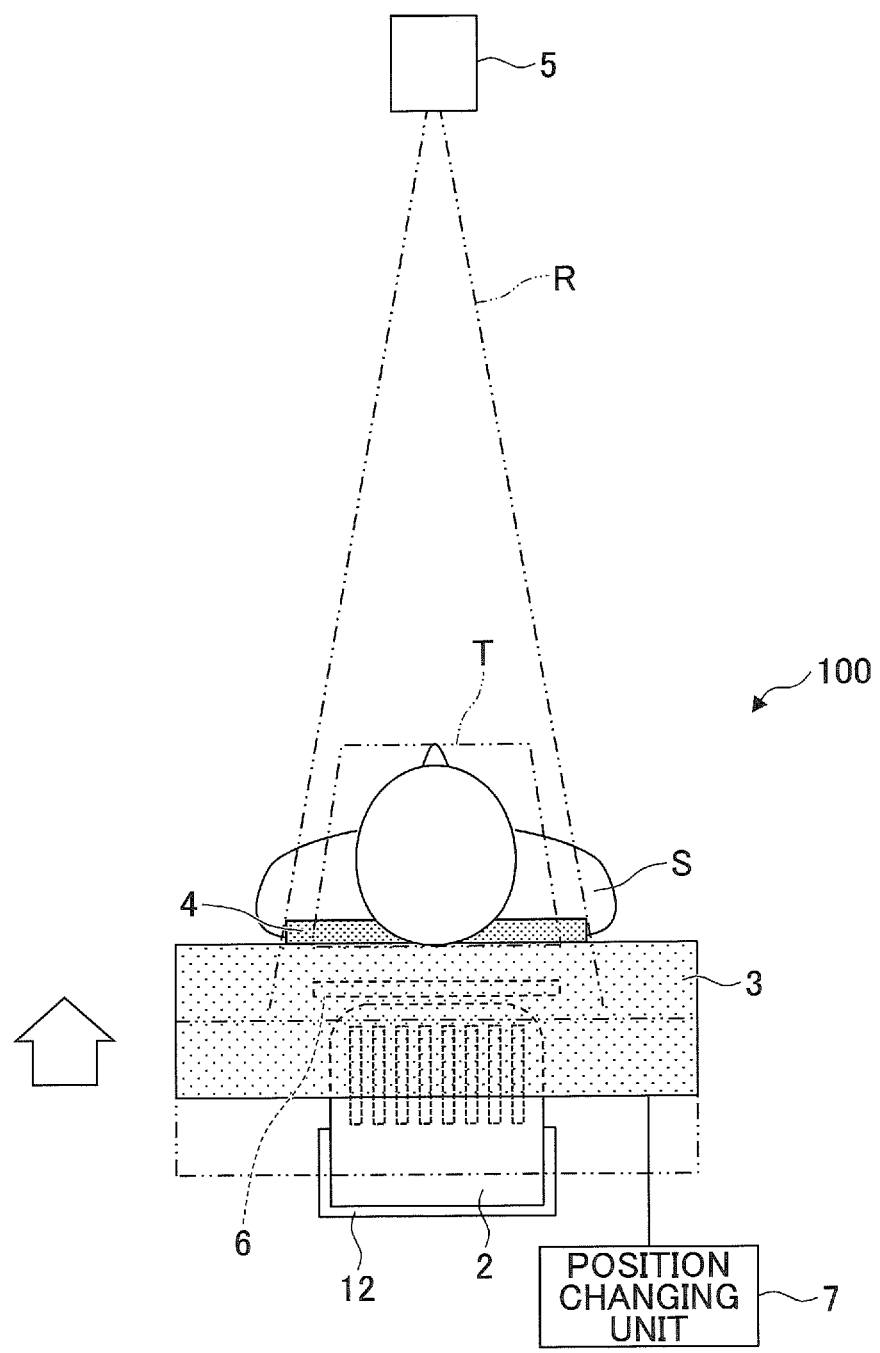
FIG. 3 is a diagram (part 3) illustrating a configuration of a biomagnetic measurement apparatus according to the first embodiment of the present invention.
Figure 4:
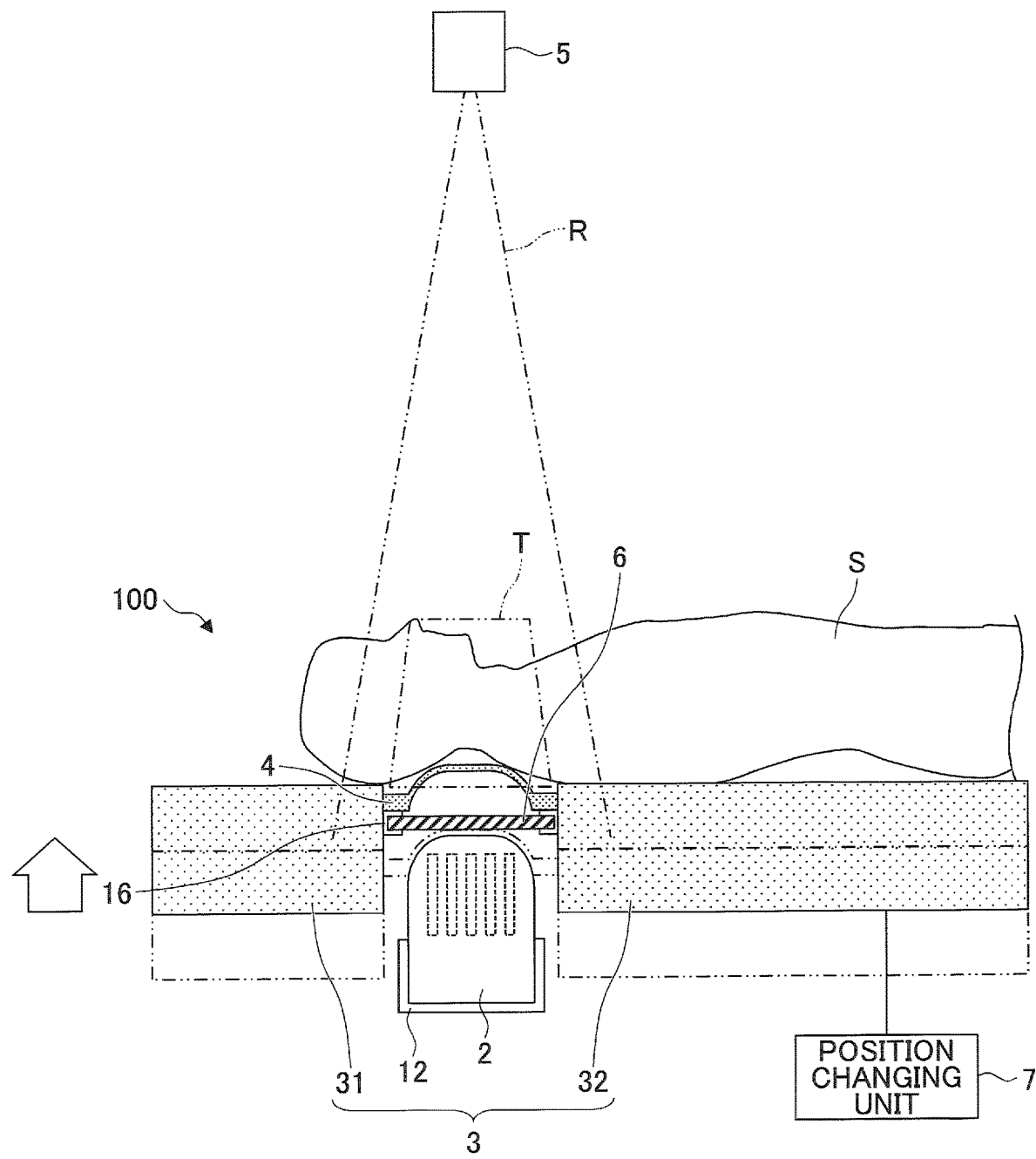
FIG. 4 is a diagram (part 4) illustrating a configuration of a biomagnetic measurement apparatus according to the first embodiment of the present invention.

First, a first embodiment will be described. FIGS. 1 to 4 are diagrams illustrating a configuration of a biomagnetic measurement apparatus 100 according to the first embodiment. FIGS. 1 and 2 illustrate the configuration when biomagnetic measurement is performed, and FIGS. 3 and 4 illustrate the configuration when radiation imaging is performed. FIGS. 1 and 3 are views seen from above the subject's head, and FIGS. 2 and 4 are views seen from the side of the subject. As illustrated in FIGS. 1 to 4, the biomagnetic measurement apparatus 100 includes a biomagnetic detecting unit 2 capable of detecting the biomagnetic field of a subject S and a table 3 on which the subject S is placed. The biomagnetic measurement apparatus 100 further includes a bridge part 4 above the biomagnetic detecting unit 2. The bridge part 4 is attachable to and detachable from the table 3, for example. The bridge part 4 may be fixed to the table 3. Furthermore, a radiation irradiation device 5 is provided above the table 3 so as to irradiate a measurement region T of the subject S. The biomagnetic measurement apparatus 100 further includes a position changing unit 7 that raises and lowers the table 3 and the bridge part 4, and a radiation detector 6 provided below the bridge part 4. The bridge part 4 is an example of a support part. For example, the biomagnetic detecting unit 2 is mounted in a mounting part 12 for the biomagnetic detecting unit 2 provided below the bridge part 4, and the radiation detector 6 is mounted in a mounting part 16 for the radiation detector 6 provided below the bridge part 4.

Hereinafter, the biomagnetic detecting unit 2, the table 3, the bridge part 4, the radiation irradiation device 5, the radiation detector 6, and the position changing unit 7 will be described respectively.

[Biomagnetic Detecting Unit 2]

Figure 5:
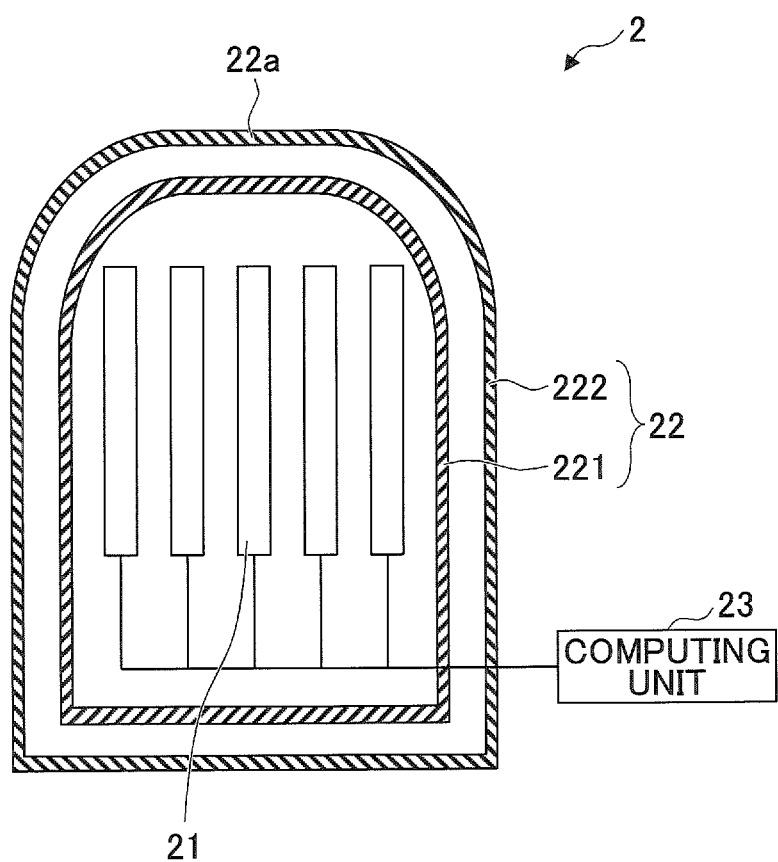
FIG. 5 is a cross-sectional view of a configuration of a biomagnetic detecting unit according to the first embodiment of the present invention.

FIG. 5 is a cross-sectional view of the configuration of the biomagnetic detecting unit 2. As illustrated in FIG. 5, the biomagnetic detecting unit 2 includes a magnetic sensor array in which a plurality of magnetic sensors 21, for detecting the biomagnetic field, is arranged in an array. The plurality of magnetic sensors 21 is held in a heat insulating container 22 having a temperature adjusting mechanism.

(Magnetic Sensor 21)

The magnetic sensor 21 detects the biomagnetic field generated from the subject. Specifically, examples of the magnetic sensor 21 include a superconducting quantum interference device (SQUID) and an optically pumped atomic magnetometer (OPAM). The SQUID sensor and optically pumped atomic magnet sensor have detection sensitivities enough to detect an extremely weak biomagnetic field of approximately $10^{-18}$ T.

In general, as illustrated in FIG. 5, a plurality of the magnetic sensors 21 is arranged in an array in the heat insulating container 22 having a temperature adjusting mechanism. The signals of the respective magnetic sensors 21 are sent to a computing unit 23 and are converted into biomagnetic information. By having a plurality of the magnetic sensors 21, not only a large amount of biomagnetic information can be obtained, but also detailed biological information can be obtained by two-dimensionally mapping the measured magnetic information, etc. Furthermore, when the magnetic sensors 21 can operate at room temperature, the temperature adjusting mechanism and the heat insulating container 22 will be unnecessary. The number and arrangement method of the magnetic sensors 21 are not particularly limited, and may be appropriately set according to the measurement region T of the subject S.

The detection signals detected by the magnetic sensors 21 are sent to the computing unit 23. The computing unit 23 generates biomagnetic information from the signals detected by the magnetic sensors 21, converts the biomagnetic information into image information, and displays the image information on a display device, etc.

(Temperature Adjusting Mechanism)

The temperature adjusting mechanism is a mechanism that adjusts the temperature of the magnetic sensors 21 to a predetermined temperature suitable for the magnetic sensors 21 to operate, and the temperature adjusting mechanism may be a known cooling device or heating device. For example, when the magnetic sensor 21 is a SQUID sensor, in order for the magnetic sensor 21 to realize a superconducting state, the magnetic sensor 21 is operated at absolute zero degree. In the present embodiment, the heat insulating container 22 fulfills a part of the function of the temperature adjusting mechanism.

(Heat Insulating Container 22)

For example, as illustrated in FIG. 5, the heat insulating container 22 includes an inner tank 221 and an outer tank 222. A plurality of magnetic sensors 21 is accommodated in the inner tank 221. A space between the inner tank 221 and the outer tank 222 is in a vacuum state, and a refrigerant such as liquid helium is supplied into the inner tank 221. Accordingly, in the biomagnetic detecting unit 2, the temperature is controlled to a temperature suitable for operation of the magnetic sensors 21.

The shape of the heat insulating container 22 is not particularly limited; however, it is preferable that the surface facing the subject S (hereinafter referred to as a leading end surface 22a) is shaped along the body surface of the measurement region T of the subject S, and the leading end surface 22a may be flat or curved. For example, as illustrated in FIG. 1 and FIG. 2, when biomagnetic measurement is performed by placing the cervical part of the subject S on the biomagnetic detecting unit 2, the shape of the leading end surface 22a preferably has a curved surface shape matching the circular arc of the cervical spinal cord.

Note that the heat insulating container 22 is not limited to the vacuum heat insulating container illustrated in FIG. 5, and the heat insulating container 22 may be formed of a foam material, etc. The heat insulating container 22 is preferably formed of a nonmagnetic material having low magnetic permeability. The heat insulating container 22 is formed of a nonmagnetic material, and, therefore, even when the heat insulating container 22 vibrates, it is possible to suppress the influence of the fluctuation of the environmental magnetism on the magnetic sensors 21. As the nonmagnetic material, plastic materials such as acrylic resin, inorganic materials such as silica and alumina, nonferrous metals such as copper, brass, aluminum, and titanium, and composite materials thereof, may be cited.

[Table 3]

The shape of the table 3 is not particularly limited as long as the subject S can be placed on and held by the table 3. For example, as illustrated in FIGS. 1 to 4, there are cases where the table 3 is formed of a plurality of region-specific tables, such as a head part table 31 for positioning the head of the subject S and a body part table 32 for positioning the body of the subject S. The biomagnetic detecting unit 2 is disposed between the head part table 31 and the body part table 32, and is provided so as to face the measurement region T of the subject S.

It is preferable that the member constituting the table 3 is formed of a nonmagnetic material having low magnetic permeability. The table 3 is formed of a nonmagnetic material, and, therefore, even if the subject S vibrates, it is possible to suppress the influence of fluctuation of environmental magnetism on the magnetic sensors 21. As the nonmagnetic material, similar to the heat insulating container 22, plastic materials such as acrylic resin, inorganic materials such as silica and alumina, nonferrous metals such as copper, brass, aluminum, and titanium, and composite materials thereof, may be cited. The table 3 supports a part of or the whole subject S, and, therefore, load resistance and impact resistance, etc., are required. For this reason, it is desirable that the table 3 is formed of metal components and engineering plastic, etc., having high mechanical strength.

[Bridge Part 4]

The bridge part 4 has a surface shape that corresponds to the surface of the biomagnetic detecting unit 2, and is provided so as to cover the biomagnetic detecting unit 2. The bridge part 4 is preferably shaped along the shape of the leading end surface 22a of the biomagnetic detecting unit 2, and it is preferable that the bridge part 4 is formed with high precision such that a gap is not formed between the biomagnetic detecting unit 2 and the bridge part 4 when the bridge part 4 is set in contact with the biomagnetic detecting unit 2. The reason that the bridge part 4 is preferably shaped along the surface shape of the biomagnetic detecting unit 2, and the bridge part 4 is preferably formed such that a gap is not formed between the biomagnetic detecting unit 2 and the bridge part 4, is to reduce the distance between the subject S and the magnetic sensor 21 as much as possible, and to measure the biomagnetic signals from the subject S as larger signals. This is because signals of the biomagnetic field are extremely weak, but if the distance between the subject S and the magnetic sensor 21 is reduced, larger signals can be expected accordingly. For example, there are cases where the signals of the biomagnetic field attenuate in inverse proportion to the square or cube of the distance.

Incidentally, the distance between the spinal cord (the origin of the biomagnetic field) of the subject S and the magnetic sensor 21 is approximately 70 mm. For this reason, even if there is some deviation, the influence on the measurement is not so large. Therefore, the shape of the bridge part 4 "shaped along the surface shape" includes a case where the shape of the bridge part 4 completely matches the surface shape of the biomagnetic detecting unit 2, and also a case where the shape of the bridge part 4 substantially matches the surface shape of the biomagnetic detecting unit 2. Note that it is preferable that the shape of the bridge part 4 completely matches the surface shape of the biomagnetic detecting unit 2.

Furthermore, the bridge part 4 may have a planar shape or a curved shape to match the shape of the leading end surface 22a of the biomagnetic detecting unit 2. The bridge part 4 moves up and down with the subject S placed thereon, and, therefore, it is desirable that the bridge part 4 has sufficient mechanical strength to withhold the load of the subject S. The cross-sectional thickness of the bridge part 4 depends on the structure and strength of the material; the thickness is preferably 1 mm to 20 mm. As an example, when the bridge part 4 is made of polycarbonate, the thickness can be set to approximately 5 mm at the portion facing the subject S in FIG. 2, and approximately 20 mm at both end portions supporting the portion facing the subject S. Furthermore, when the bridge part 4 is made of glass fiber reinforced plastic (GFRP), the cross-sectional thickness of the bridge part 4 can be set to approximately 1 mm to 3 mm at the portion facing the subject S in FIG. 2, and approximately 5 mm to 10 mm at both end portions supporting the portion facing the subject S.

It is preferable that the member constituting the bridge part 4 is formed of a nonmagnetic material having low magnetic permeability. The bridge part 4 is formed of a nonmagnetic material, and, therefore, even if the subject S vibrates, it is possible to suppress the influence of the fluctuation of the environmental magnetism on the magnetic sensor 21. As the nonmagnetic material, similar to the heat insulating container 22 and the table 3, plastic materials such as acrylic resin, inorganic materials such as silica and alumina, nonferrous metals such as copper, brass, aluminum, and titanium, and composite materials thereof, may be cited. The bridge part 4 may be fabricated by performing a cutting process, a bending process, or an injection molding process, etc., on the material.

[Position Changing Unit 7]

The position changing unit 7 raises and lowers the table 3 and the bridge part 4 in synchronization with each other. The raising and lowering mechanism may be manual or electric, and in particular, an electric raising and lowering mechanism using a hydraulic cylinder and an electric pump is useful. Regarding the raising and lowering of the table 3, the entire table 3 may be raised and lowered, or only a part of the table 3, for example, the top board of the table 3, may be raised and lowered.

Figure 6A:
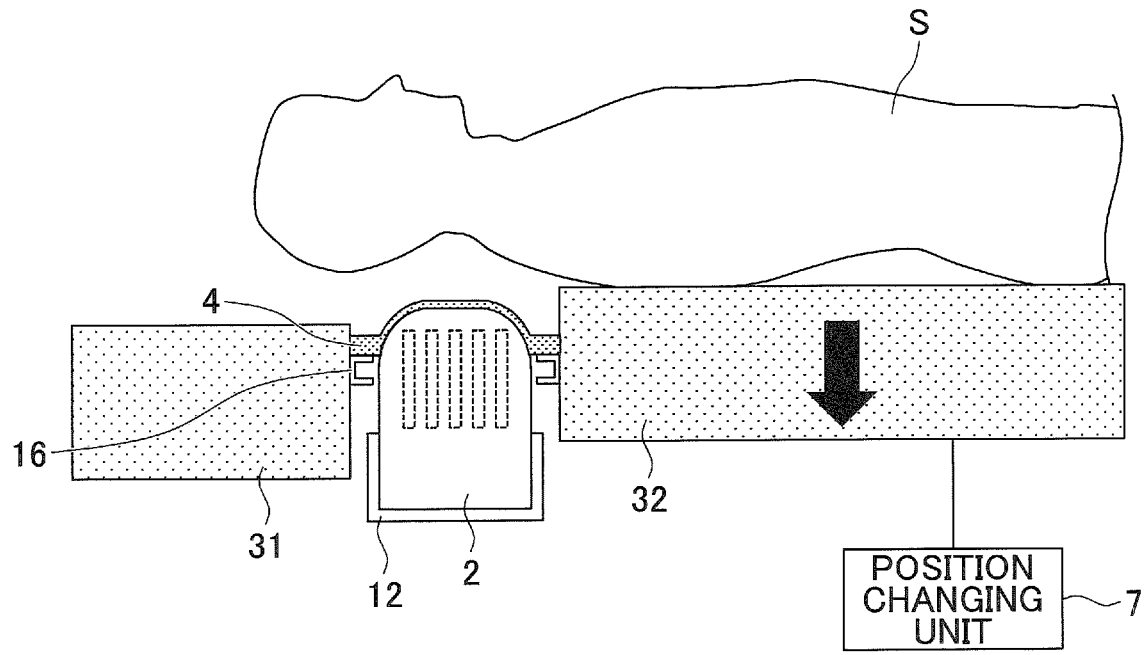
FIGS. 6A and 6B are diagrams illustrating functions of a position changing unit according to the first embodiment of the present invention.
Figure 6B:
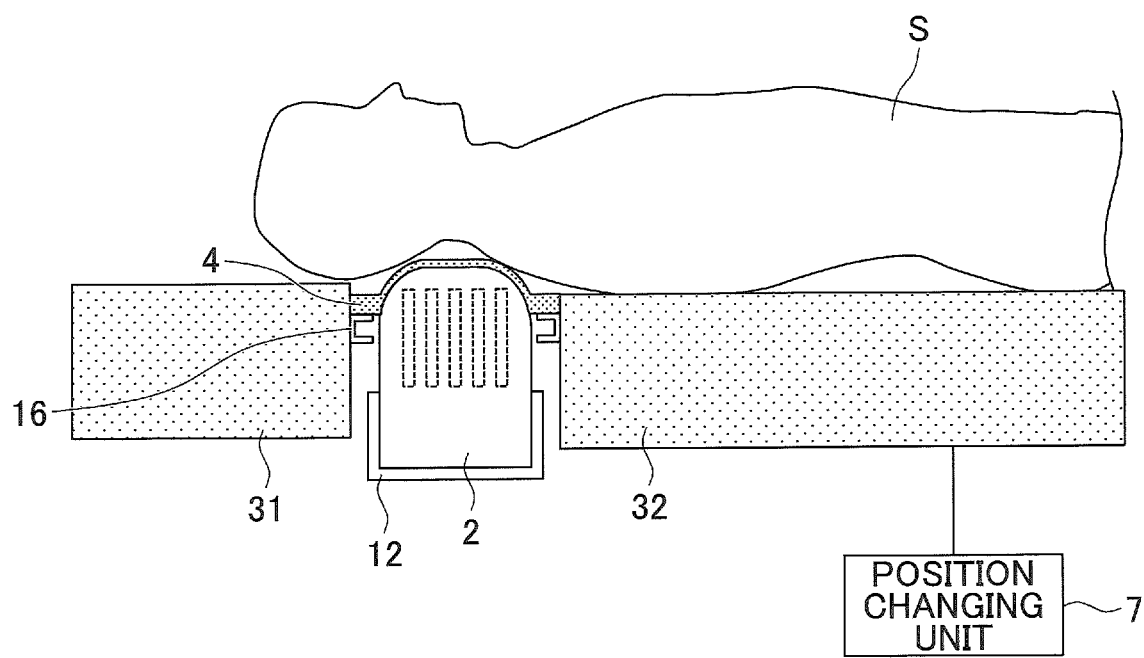

The head part table 31 and the body part table 32 may be fixed to each other via the bridge part 4. In this case, the position changing unit 7 can raise and lower the head part table 31 and the body part table 32 in synchronization with each other as a single unit. The bridge part 4 may be connected to either the head part table 31 or the body part table 32, and the position changing unit 7 may individually raise and lower each of the bridge part 4, the head part table 31, and the body part table 32. When the relative positions of the bridge part 4, the head part table 31, and the body part table 32 can be changed, for example, as illustrated in FIG. 6A, it is possible to lower only the body part table 32, and as illustrated in FIG. B, the adhesion between the measurement region T of the subject S and the bridge part 4 can be improved. After lowering only the body part table 32, for fine adjustment, it is possible to raise or lower one of or both of the bridge part 4 and the head part table 31.

[Radiation Irradiation Device 5]

A known radiation irradiation device 5 may be used as long as the radiation irradiation device 5 can irradiate radiation that can be radiated to a living body. In the present invention, "radiation" is not limited to generally used simple x-rays, but is a comprehensive concept including α-rays, β rays, and γ rays, etc., which are beams made by particles (including photons) emitted by radioactive decay, and also beams having energy greater than or equal to the aforementioned beams, for example, particle beams and cosmic rays, etc. Considering high versatility, it is preferable to use simple x-rays as the radiation.

[Radiation Detector 6]

The radiation detector 6 is mounted in the mounting part 16, in a state in which the table 3 and the bridge part 4 are raised, and a gap is formed between the bridge part 4 and the biomagnetic detecting unit 2. The radiation detector 6 acquires radiation R that has been transmitted through the measurement region T of the subject S, as a morphological image that is digital image data.

The signals detected by the radiation detector 6 are sent to the computing unit. In the computing unit, a morphological image is generated from the signals detected by the radiation detector 6, and the morphological image is converted into image information and is displayed on a display device For example, a flat panel detector (FPD) may be used as the radiation detector 6. As the FPD, there are a so-called direct conversion method in which charges are generated by a detection element according to the dose of irradiated radiation, and the charges are converted into electric signals; and a so-called indirect conversion method in which irradiated radiation is converted into electromagnetic waves of another wavelength such as visible light, with a scintillator, etc., and then charges are generated by a photoelectric conversion element such as a photodiode, etc., according to the energy of the converted and irradiated electromagnetic waves, and the charges are converted into electric signals.

Furthermore, a so-called imaging plate (hereinafter referred to as "IP"), in which a film coated with photostimulable phosphor powder is housed in a casing referred to as a cassette, may also be suitably used. The radiation transmitted through the measurement region T of the subject S is irradiated onto the imaging plate, and the energy of the radiation is stored in the photostimulable phosphor. Subsequently, the imaging plate is irradiated with laser beams of a particular wavelength in a reading device, and by reading the light amount by a scanner, the morphological image can be acquired as digital image data.

In the biomagnetic measurement apparatus 100 configured as described above, the biomagnetic measurement using the biomagnetic detecting unit 2, and the capturing of a simple x-ray image using the radiation irradiation device 5 and the radiation detector 6, are performed. Either one of these processes may be performed first. The height of the table 3 and the bridge part 4 differ between the state illustrated in FIGS. 1 and 2 and the state illustrated in FIG. 3 and FIG. 4; the movement of the table 3 and the bridge part 4, in this case, the raising and lowering, is operated by the position changing unit 7.

Biomagnetic measurement is performed in the state illustrated in FIGS. 1 and 2. That is, in a state where the bridge part 4 is brought into close contact with the biomagnetic detecting unit 2, the measurement region T of the subject S is supported on the bridge part 4, and the other regions of the subject S are placed on the table 3, the biomagnetic detecting unit 2 measures biomagnetic in the measurement region T.

The capturing of the simple x-ray image is performed in the state illustrated in FIGS. 3 and 4. That is, in a state in which the table 3 and the bridge part 4 have been synchronously raised by the position changing unit 7 while the subject S is placed on the table 3 and the bridge part 4, radiation is emitted from the radiation irradiation device 5, and the radiation transmitted through the measurement region T is detected by the radiation detector 6. In this state, there is a gap between the biomagnetic detecting unit 2 and the bridge part 4, the radiation detector 6 is mounted in the mounting part 16 in the gap, the measurement region T of the subject S is supported on the bridge part 4, and the other regions of the subject S are placed on the table 3. After capturing a simple x-ray image, the radiation detector 6 is removed from the mounting part 16, and the position changing unit 7 lowers the table 3 and the bridge part 4 in synchronization with each other.

According to the biomagnetic measurement apparatus 100 of the present embodiment, measurement of biomagnetic using the biomagnetic detecting unit 2 and acquisition of a morphological image using the radiation detector 6 can be performed while maintaining the posture of the subject S. Therefore, it is possible to precisely superimpose the biomagnetic detection result obtained from the biomagnetic detecting unit 2 and a morphological image, which is digital image data of the simple x-ray image obtained from the radiation detector 6.

Furthermore, in the biomagnetic measurement apparatus 100, the radiation detector 6 can be removed at the time of biomagnetic measurement. Therefore, whichever one of FPD or IP is used as the radiation detector 6, the influence on the biomagnetic measurement by the radiation detector 6 can be eliminated. Comparing the FPD and the IP, the FPD, which does not require an indirect reading device, is preferable, because the FPD is easy to handle and convenient. Because commercially available FPDs include many magnetic materials in the control electronic circuit and the batteries, etc., it is extremely preferable to remove the FPD at the time of biomagnetic measurement. Furthermore, commercially available FPDs are flat, and, therefore, it is difficult to superimpose measurement results with excellent precision, when used in combination with the biomagnetic detecting unit 2 having the curved leading end surface 22a. That is, a case where the shape of the measurement region T of the subject S is on the plane of the FPD, is different from a case where the shape of the measurement region T of the subject S is on the leading end surface 22a of the biomagnetic detecting unit 2, and therefore the morphological image obtained by the FPD and is different from the shape of the measurement region T on the leading end surface 22a. Therefore, in the case of using a conventional biomagnetic measurement apparatus, deviation easily occurs between the morphological image captured by using the FPD and the biomagnetic measurement result obtained from the biomagnetic detecting unit 2. Conversely, if the biomagnetic measurement apparatus 100 according to the present embodiment is used, such a deviation can be eliminated.

In order to further improve the superimposing precision between the biomagnetic measurement result obtained from the biomagnetic detecting unit 2 and the morphological image obtained from the radiation detector 6, it is preferable to use a marker that can be detected by both the radiation detector 6 and the biomagnetic detecting unit 2. An example of such a marker is an electromagnetic coil. In the radiation detector 6, the cable of the coil part included in the electromagnet coil appears, and a magnetic field generated by the electric signals supplied to the electromagnet coil is detected in the biomagnetic detecting unit 2. By superimposing the detection results so that the positions of the markers such as electromagnet coils coincide with each other, superposition with higher precision becomes possible. The electromagnet coil may be embedded in the bridge part 4. In the case where the electromagnet coil is adhered to the surface of the bridge part 4, the electromagnetic coil can come into contact with the subject S; however, by embedding the electromagnet coil in the bridge part 4, it is possible to suppress physical interference with the subject S.

The mounting part 12 and the mounting part 16 contribute to maintaining the relative positions of the biomagnetic detecting unit 2 and the radiation detector 6. By maintaining the relative positions of the biomagnetic detecting unit 2 and the radiation detector 6, even when a position specifying means such as a marker for specifying the mutual position information is not provided, it is possible to precisely superimpose the biomagnetic detection result obtained from the biomagnetic detecting unit 2 and the morphological image obtained from the radiation detector 6. However, either one of or both of the mounting part 12 and the mounting part 16 may not be provided.

The size of the radiation detector 6 is not particularly limited, and may be any size as long as the size corresponds to the measurement region T of the subject S. The radiation detector 6 is preferably smaller than the irradiation region of the radiation irradiated from the radiation irradiation device 5, and the relative distance between the radiation irradiation device 5 and the subject S can also be appropriately adjusted.

In the present embodiment, the FPD and the IP are exemplified as the radiation detector 6, and a simple x-ray apparatus is exemplified as the radiation irradiation device 5; however, a computed tomography (CT) apparatus, etc., can also be suitably used. A CT apparatus scans a subject with radiation, and performs image processing on the transmitted radiation amount in a computer, to obtain an image of the internal structure of a subject, that is, the CT apparatus is a diagnostic apparatus including both a radiation detector and a radiation irradiation device.

Second Embodiment

Figure 7:
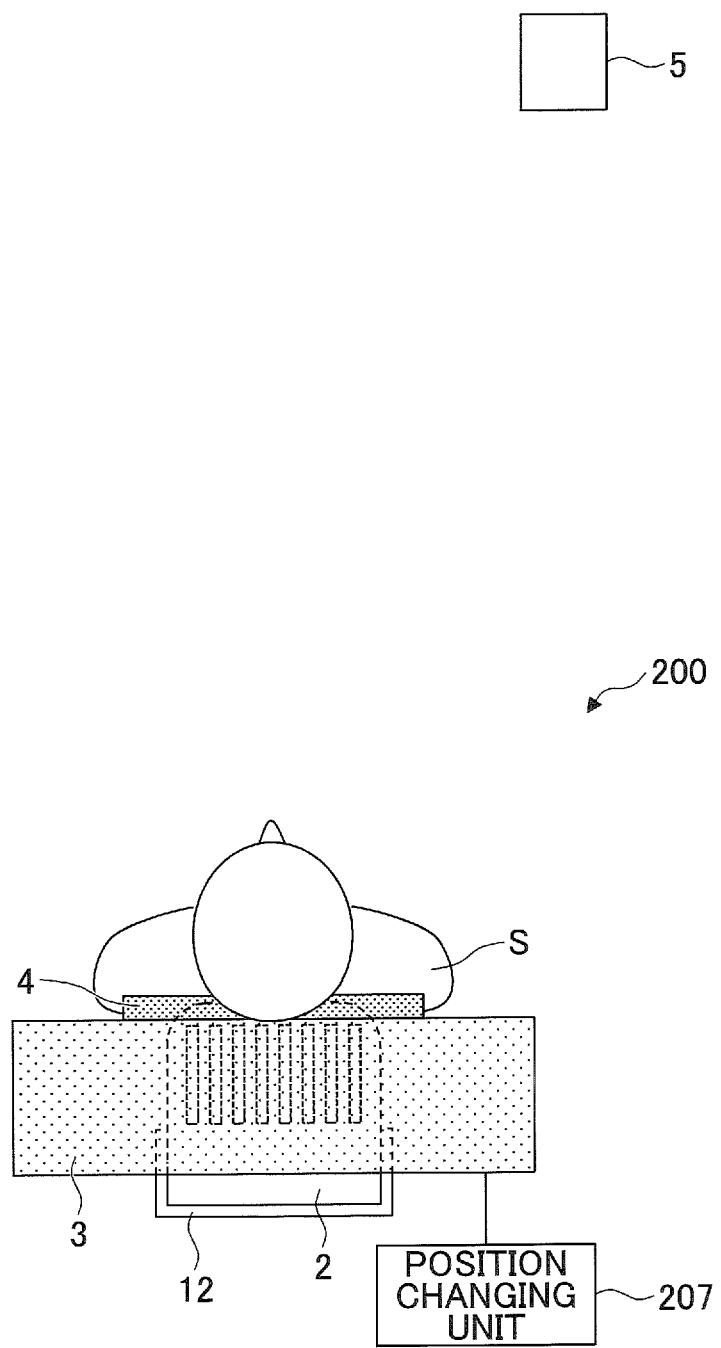
FIG. 7 is a diagram (part 1) illustrating a configuration of a biomagnetic measurement apparatus according to a second embodiment of the present invention.
Figure 8:
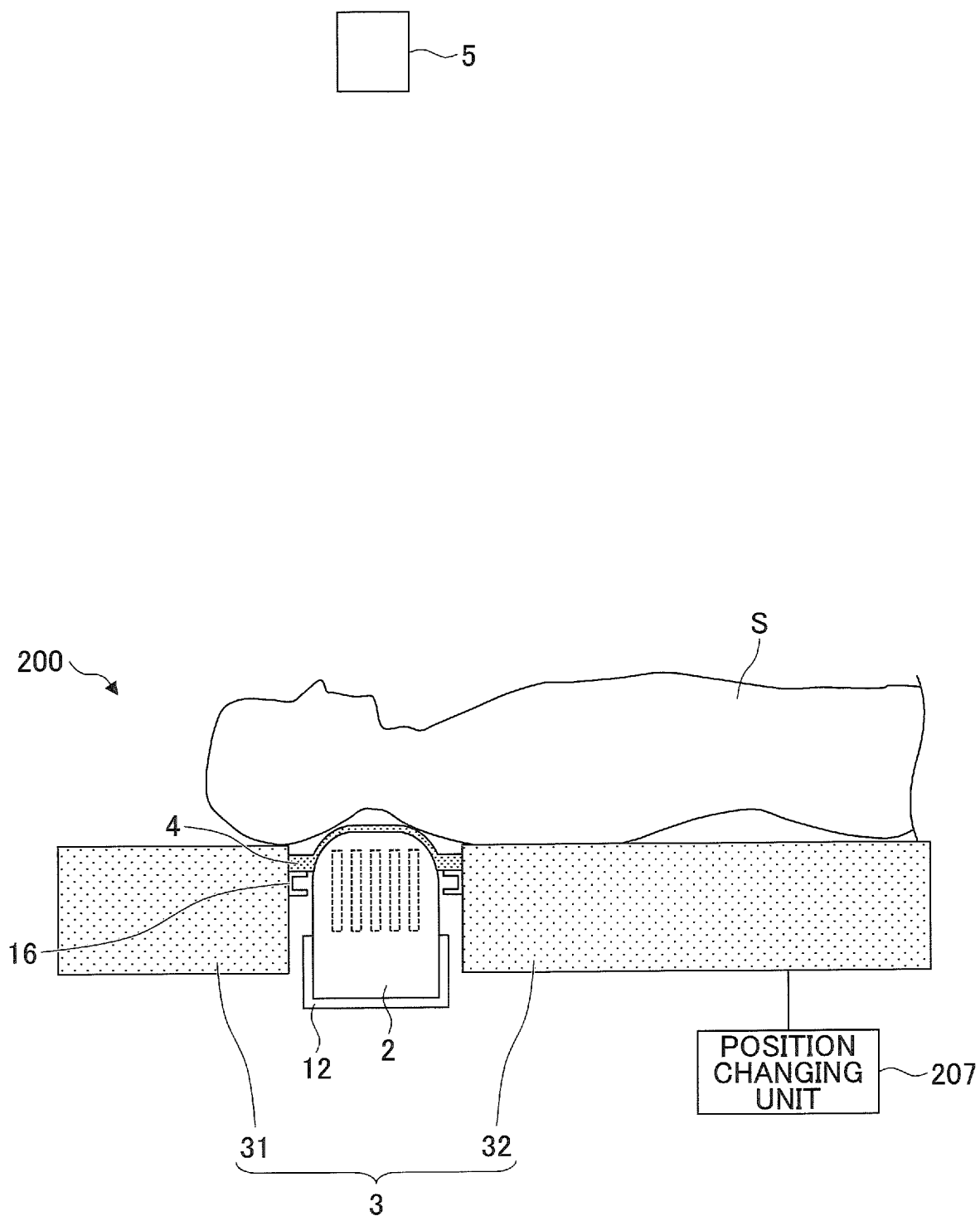
FIG. 8 is a diagram (part 2) illustrating a configuration of a biomagnetic measurement apparatus according to the second embodiment of the present invention.
Figure 9:
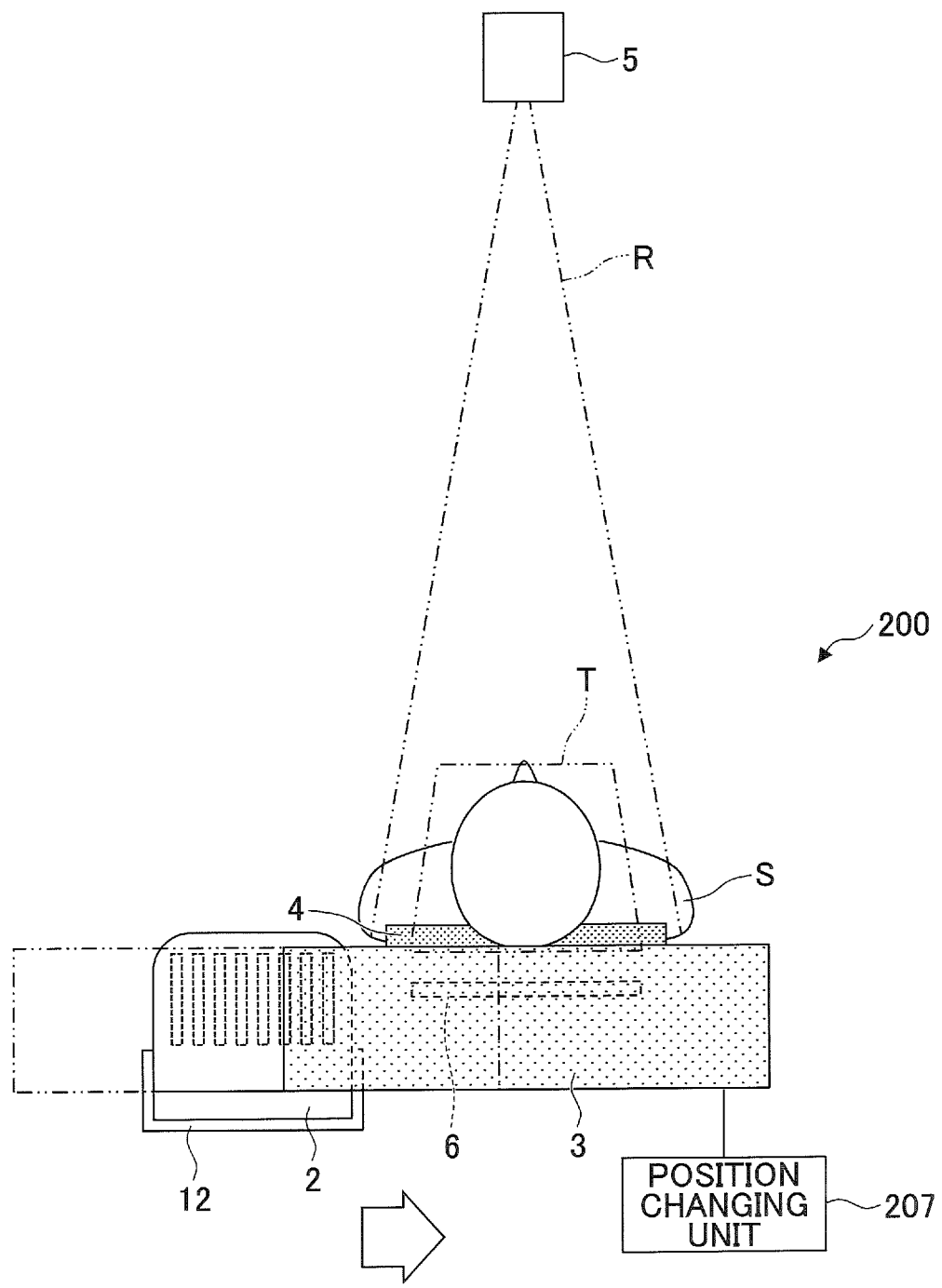
FIG. 9 is a diagram (part 3) illustrating a configuration of a biomagnetic measurement apparatus according to the second embodiment of the present invention.
Figure 10:
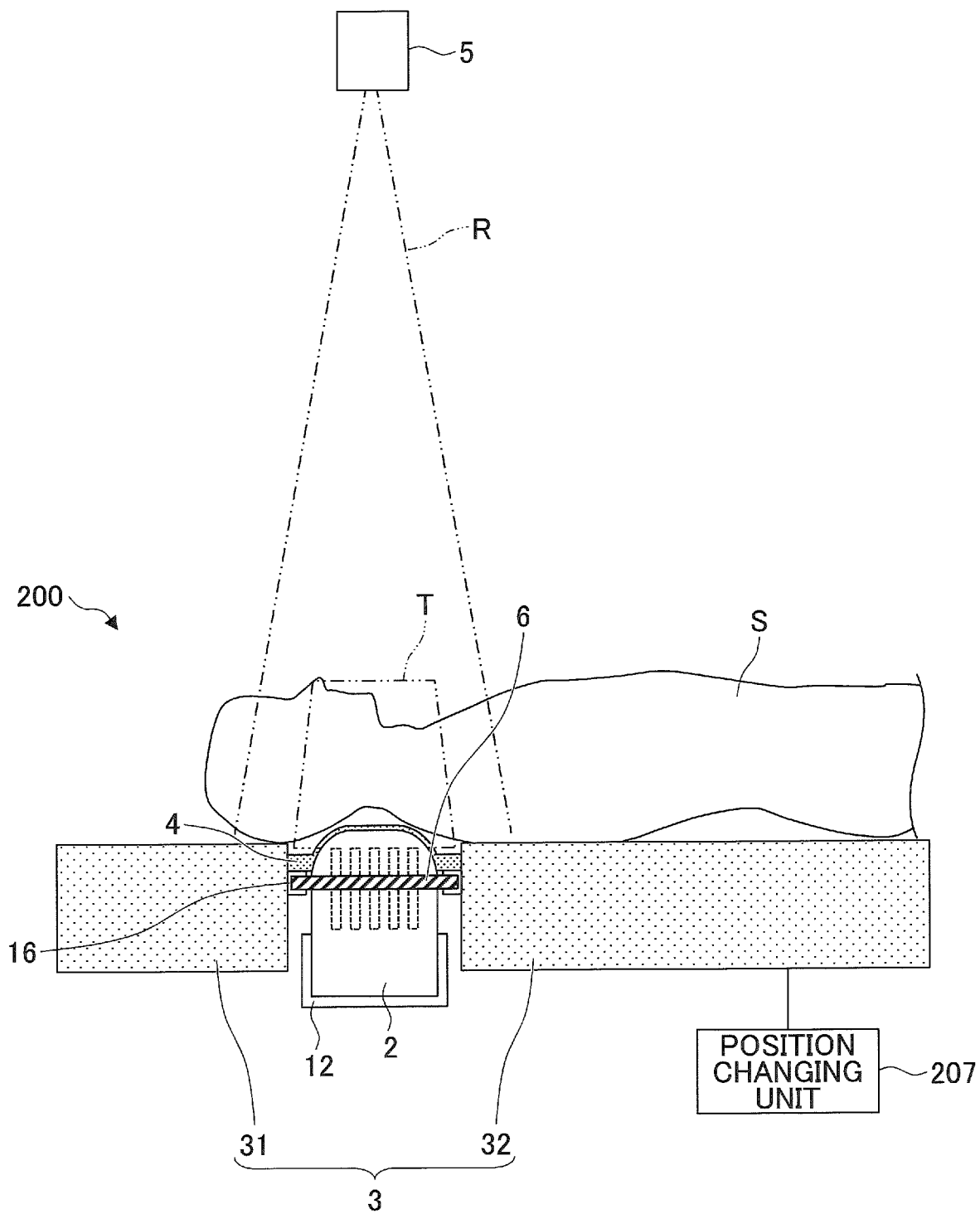
FIG. 10 is a diagram (part 4) illustrating a configuration of a biomagnetic measurement apparatus according to the second embodiment of the present invention.

Next, a second embodiment will be described. FIGS. 7 to 10 are diagrams illustrating a configuration of a biomagnetic measurement apparatus 200 according to the second embodiment. FIGS. 7 and 8 illustrate the configuration when biomagnetic measurement is performed, and FIGS. 9 and 10 illustrate the configuration when radiation imaging is performed. FIGS. 7 and 9 are views seen from above the subject's head, and FIGS. 8 and 10 are views seen from the side of the subject. As illustrated in FIGS. 7 to 10, the biomagnetic measurement apparatus 200 includes a position changing unit 207 instead of the position changing unit 7 according to the first embodiment. Furthermore, the radiation irradiation device 5 is not provided directly above the biomagnetic detecting unit 2 in the vertical direction, but is provided at a position deviated from a position directly above the biomagnetic detecting unit 2 in the vertical direction. The other configurations are the same as in the first embodiment.

The position changing unit 7 raises and lowers the table 3 and the bridge part 4; however, the position changing unit 207 synchronously moves the table 3 and the bridge part 4 in the horizontal direction. A horizontal movement mechanism may be manual or electric. For example, various known horizontal movement mechanisms such as a bearing, a roller, a belt conveyor, a guide rail, a slide rail, a linear motion pusher, a ball screw linear motion mechanism, or a combination thereof may be used. With respect to the movement of the table 3, the entire table 3 may be moved, or only a part of the table 3, for example the top board of the table 3, may be moved. As described above, in the second embodiment, the moving direction of the table 3 and the bridge part 4 is different from that in the first embodiment.

In the biomagnetic measurement apparatus 200 configured as described above, the biomagnetic measurement using the biomagnetic detecting unit 2 and the capturing of a simple x-ray image using the radiation irradiation device 5 and the radiation detector 6, are performed. Whichever one of these operations may be performed first. The positions of the table 3 and the bridge part 4 differ between the state illustrated in FIGS. 7 and 8 and the state illustrated in FIGS. 9 and 10; the movement of the table 3 and the bridge part 4, in this case, a horizontal movement in a direction to the side of the body, is operated by the position changing unit 207.

Biomagnetic measurement is performed in the state illustrated in FIGS. 7 and 8. That is, similar to the first embodiment, the bridge part 4 is brought into close contact with the biomagnetic detecting unit 2, the measurement region T of the subject S is supported on the bridge part 4, the other parts of the subject S are placed on the table 3, and the biomagnetic detecting unit 2 measures the biomagnetic field of the measurement region T.

The capturing of a simple x-ray image is performed in the state illustrated in FIGS. 9 and 10. That is, in a state in which the table 3 and the bridge part 4 have been synchronously moved by the position changing unit 207 to the position immediately below the radiation irradiation device 5 with the subject S placed on the table 3 and the bridge part 4, radiation is emitted from the radiation irradiation device 5, and the radiation transmitted through the measurement region T is detected by the radiation detector 6. In this state, there is a space below the bridge part 4, and the radiation detector 6 is mounted in the mounting part 16 in this space, the measurement region T of the subject S is supported on the bridge part 4, and the other regions of the subject S are placed on the table 3. After capturing a simple x-ray image, the radiation detector 6 is removed from the mounting part 16, and the position changing unit 207 horizontally moves the table 3 and the bridge part 4 in synchronization with each other to the original position.

When the position changing unit 207 includes a caster attached to the table 3, the table 3 is separated from the biomagnetic detecting unit 2 while maintaining the posture of the subject, and the table 3 is moved to another room in which, for example, a CT apparatus or an MRI diagnostic apparatus is installed, and detailed image capturing may be performed in the other room. Alternatively, a CT apparatus or an MRI apparatus may be brought in, and image capturing may be performed on the spot. When the CT apparatus is used, the CT apparatus functions as the radiation irradiation device 5 and the radiation detector 6.

Third Embodiment

Figure 11:
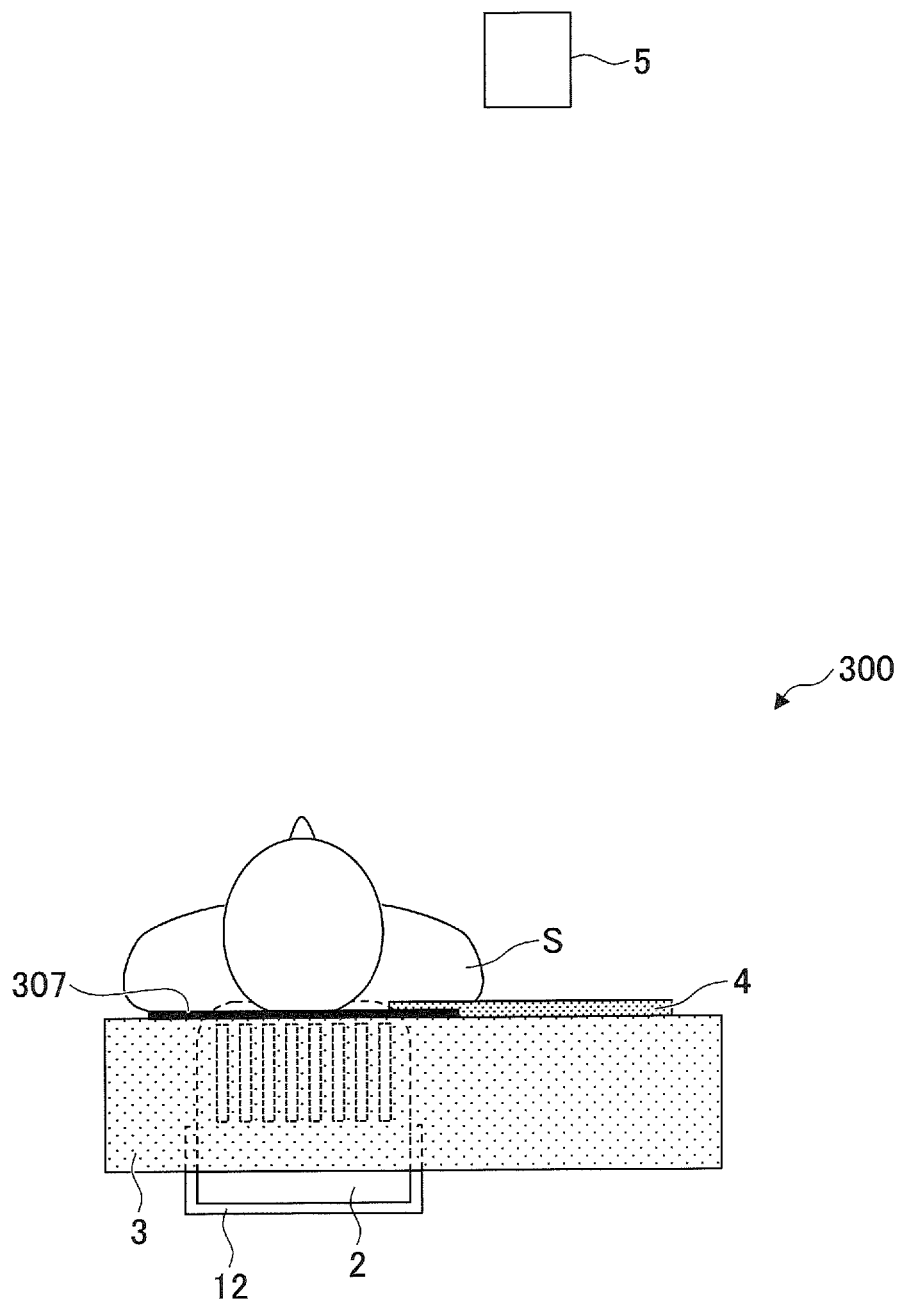
FIG. 11 is a diagram (part 1) illustrating a configuration of a biomagnetic measurement apparatus according to a third embodiment of the present invention.
Figure 13:
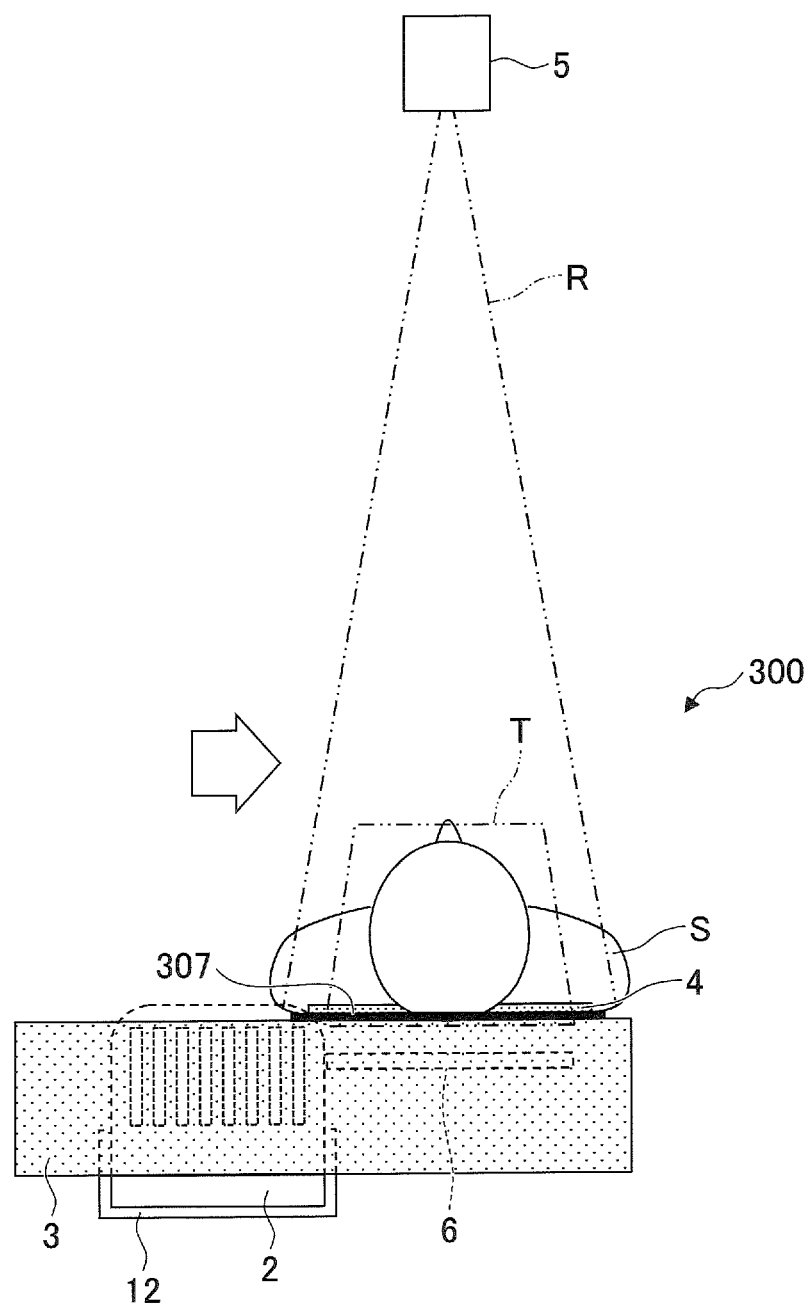
FIG. 13 is a diagram (part 3) illustrating a configuration of a biomagnetic measurement apparatus according to the third embodiment of the present invention.
Figure 14:
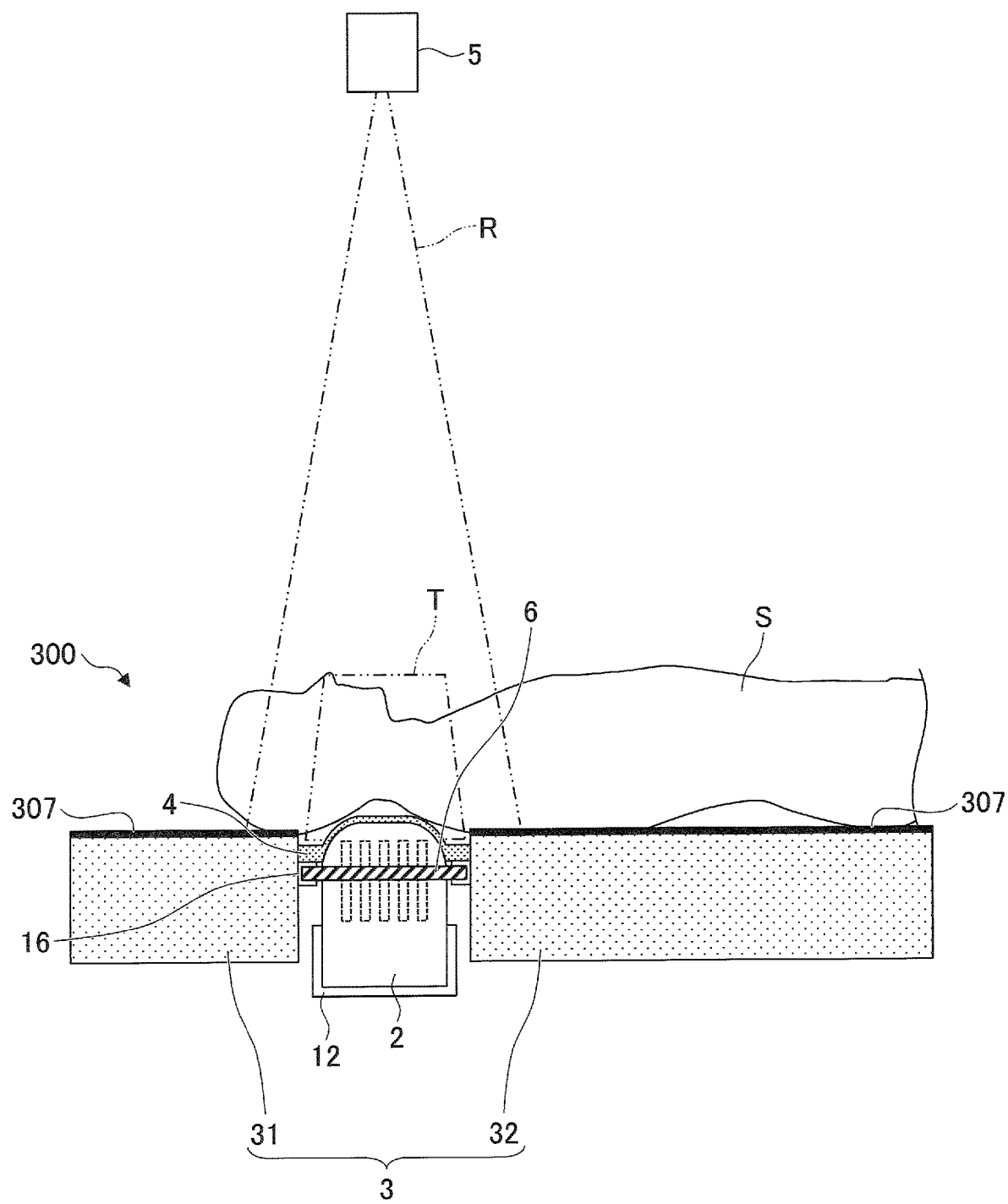
FIG. 14 is a diagram (part 4) illustrating a configuration of a biomagnetic measurement apparatus according to the third embodiment of the present invention.

Next, a third embodiment will be described. FIGS. 11 to 14 are diagrams illustrating a configuration of a biomagnetic measurement apparatus 300 according to the third embodiment. FIGS. 11 and 12 illustrate the configuration when biomagnetic measurement is performed, and FIGS. 13 and 14 illustrate the configuration when radiation imaging is performed. FIGS. 11 and 12 are views seen from above the subject's head, and FIGS. 13 and 14 are views seen from the side of the subject. As illustrated in FIGS. 11 to 14, the biomagnetic measurement apparatus 300 includes a position changing unit 307 instead of the position changing unit 7 according to the first embodiment. Furthermore, the radiation irradiation device 5 is not provided directly above the biomagnetic detecting unit 2 in the vertical direction, but is provided at a position deviated from a position directly above the biomagnetic detecting unit 2 in the vertical direction. Furthermore, the bridge part 4 is not provided above the biomagnetic detecting unit 2, but is provided below the radiation irradiation device 5 in the vertical direction. The mounting part 16 and the radiation detector 6 are also provided below the radiation irradiation device 5 in the vertical direction. The other configurations are the same as in the first embodiment.

The position changing unit 7 and the position changing unit 207 move the table 3 and the bridge part 4; however, the position changing unit 307 moves the subject S in the horizontal direction. For example, in the case where a movable top plate is provided on the table 3, the position changing unit 307 moves the top plate, on which the subject S is placed, while the main body of the table 3 is fixed, thereby horizontally moving the subject S. Furthermore, if it is possible to move the subject S in the horizontal direction while maintaining the posture of the subject S, for example, a cloth or a film may be provided as the position changing unit 307 between the table 3 and the subject S, and the subject S can be moved by sliding the position changing unit 307 on the table 3.

In the biomagnetic measurement apparatus 300 configured as described above, the biomagnetic measurement using the biomagnetic detecting unit 2 and the capturing of a simple x-ray image using the radiation irradiation device 5 and the radiation detector 6, are performed. Whichever one of these operations may be performed first. The position of the subject S differs between the state illustrated in FIGS. 11 and 12 and the state illustrated in FIGS. 13 and 14; the movement of the subject S, in this case, a horizontal movement in a direction to the side of the body, is operated by the position changing unit 307.

The biomagnetic measurement is performed in the state illustrated in FIGS. 11 and 12. That is, in a state in which the measurement region T of the subject S closely contacts the biomagnetic detecting unit 2 and the other regions of the subject S are placed on the table 3, the biomagnetic detecting unit 2 measures the biomagnetic field of the measurement region T.

The capturing of a simple x-ray image is performed in the state illustrated in FIGS. 13 and 14. That is, in a state in which the position changing unit 307 has moved the subject S immediately below the radiation irradiation device 5, radiation is emitted from the radiation irradiation device 5, and the radiation transmitted through the measurement region T is detected by the radiation detector 6. In this state, there is a space below the bridge part 4, and the radiation detector 6 is mounted in the mounting part 16 in this space, the measurement region T of the subject S is supported on the bridge part 4, and the other regions of the subject S are placed on the table 3. After capturing a simple x-ray image, the radiation detector 6 is removed from the mounting part 16, and the position changing unit 307 horizontally moves the subject S to the original position.

The same effect as in the second embodiment can be obtained also in the third embodiment. Furthermore, the bridge part 4 is disposed so as to be deviated from the position directly above the biomagnetic detecting unit 2, and therefore biomagnetic measurement can be performed with high precision without removing the bridge part 4.

<Biomagnetic Measurement Method using Biomagnetic Measurement Apparatus 100>

Figure 15:
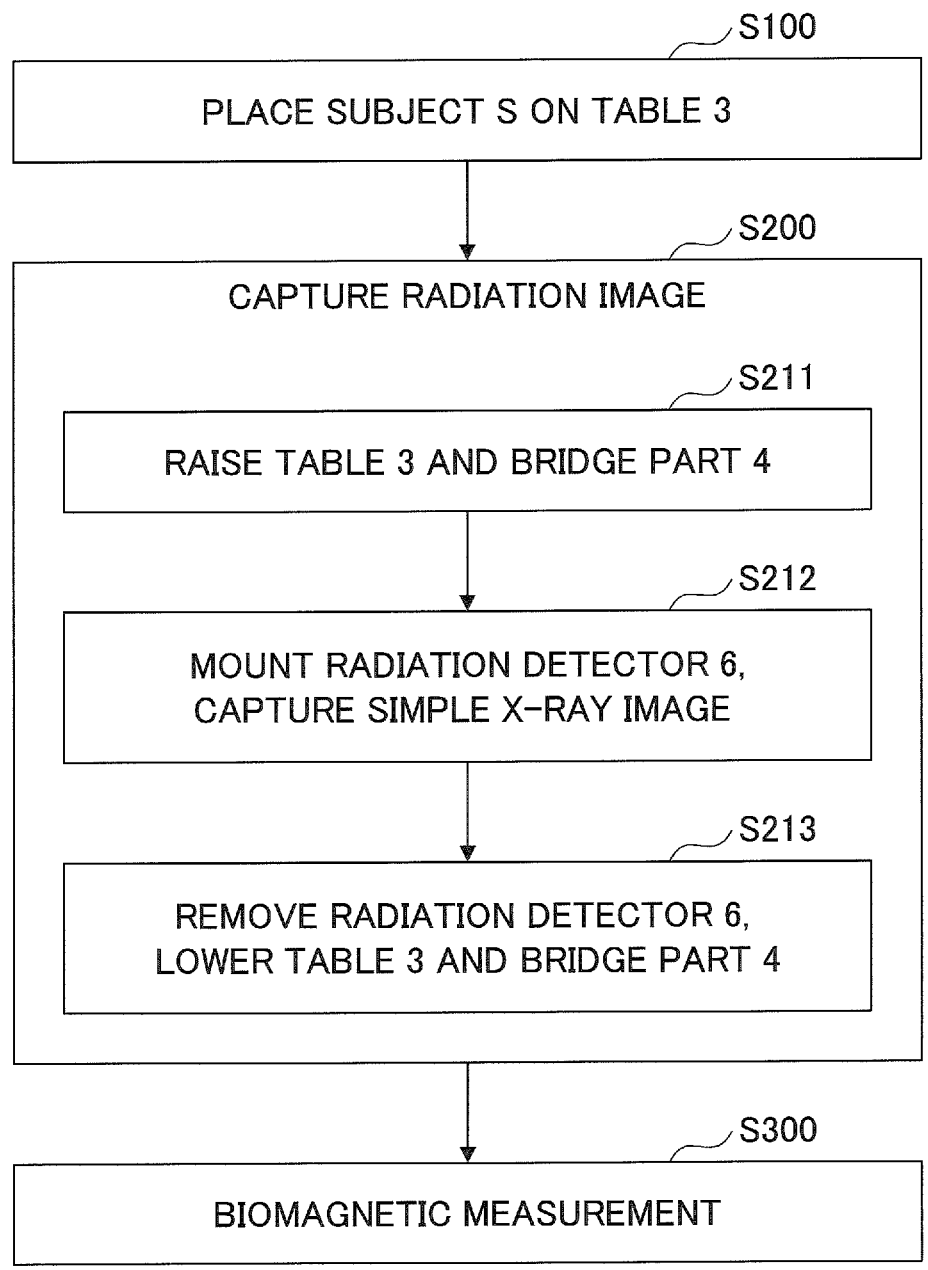
FIG. 15 is a flowchart illustrating a biomagnetic measurement method using the biomagnetic measurement apparatus according to the first embodiment of the present invention.

Next, a biomagnetic measurement method using the biomagnetic measurement apparatus 100 will be described. FIG. 15 is a flowchart illustrating a biomagnetic measurement method using the biomagnetic measurement apparatus 100. In this biomagnetic measurement method, radiation imaging and biomagnetic measurement of the spinal cord of a subject (human) S is performed.

First, the subject S is placed in a supine position on the table 3, and stands by at a position where the spinal cord of the subject S comes immediately above the biomagnetic detecting unit 2 (step S100).

Next, radiation imaging is performed (step S200). Specifically, an examiner such as a medical radiology technician operates the position changing unit 7 to synchronously raise the table 3 and the bridge part 4 while the subject S is placed on the table 3 and the bridge part 4 (step S211). Subsequently, the examiner inserts the radiation detector 6 into the mounting part 16 in the gap formed between the bridge part 4 and the biomagnetic detecting unit 2, operates an operation unit for the radiation irradiation device 5, radiation is irradiated from the irradiation device 5 toward the subject S, and a simple x-ray image of the subject S is captured by the radiation detector 6 (step S212). Subsequently, the radiation detector 6 is removed from the mounting part 16, and the position changing unit 7 is operated to synchronously lower the table 3 and the bridge part 4 while the subject S is placed on the table 3 and the bridge part 4 (step S213).

Next, biomagnetic measurement is performed (step S300). Specifically, the spinal cord evoked magnetic field, which is the detection result from the biomagnetic detecting unit 2, is acquired.

Figure 16:
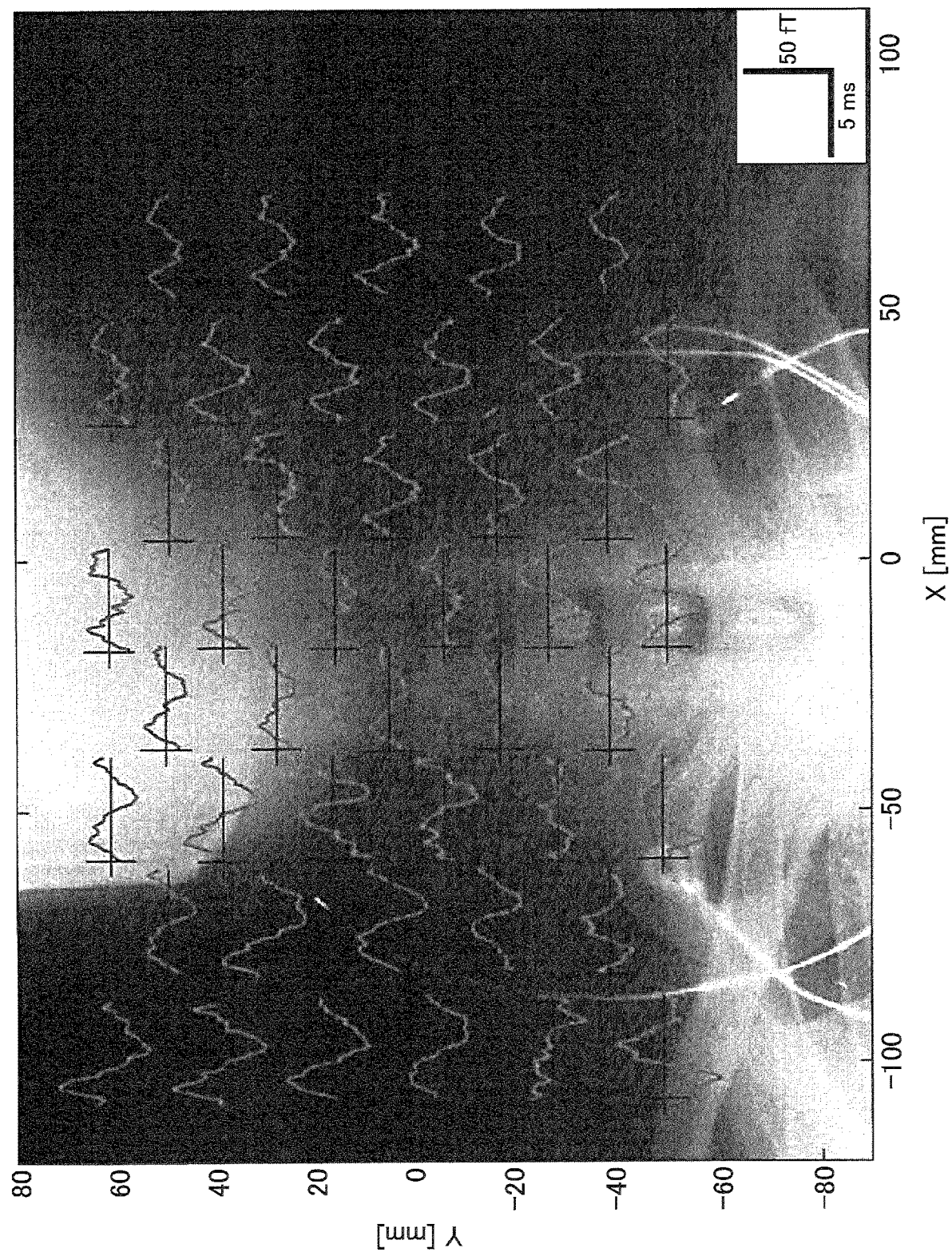
FIG. 16 is a diagram illustrating an example of a measurement result obtained by superimposing a biological information measurement result and a simple x-ray image according to the first embodiment of the present invention.

The measurement result (biological information measurement result) of the spinal cord evoked magnetic field obtained in step 5300, is superimposed on the simple x-ray image acquired in step S200, and is displayed on a display device. FIG. 16 illustrates an example of a measurement result obtained by superimposing a biological information measurement result and a simple x-ray image of a human on each other. As can be seen from FIG. 16, it is possible to obtain biological information, which is obtained by superimposing a simple x-ray image of the spinal cord and a spinal cord evoked magnetic field map, with high precision by one measurement operation.

Figure 17:
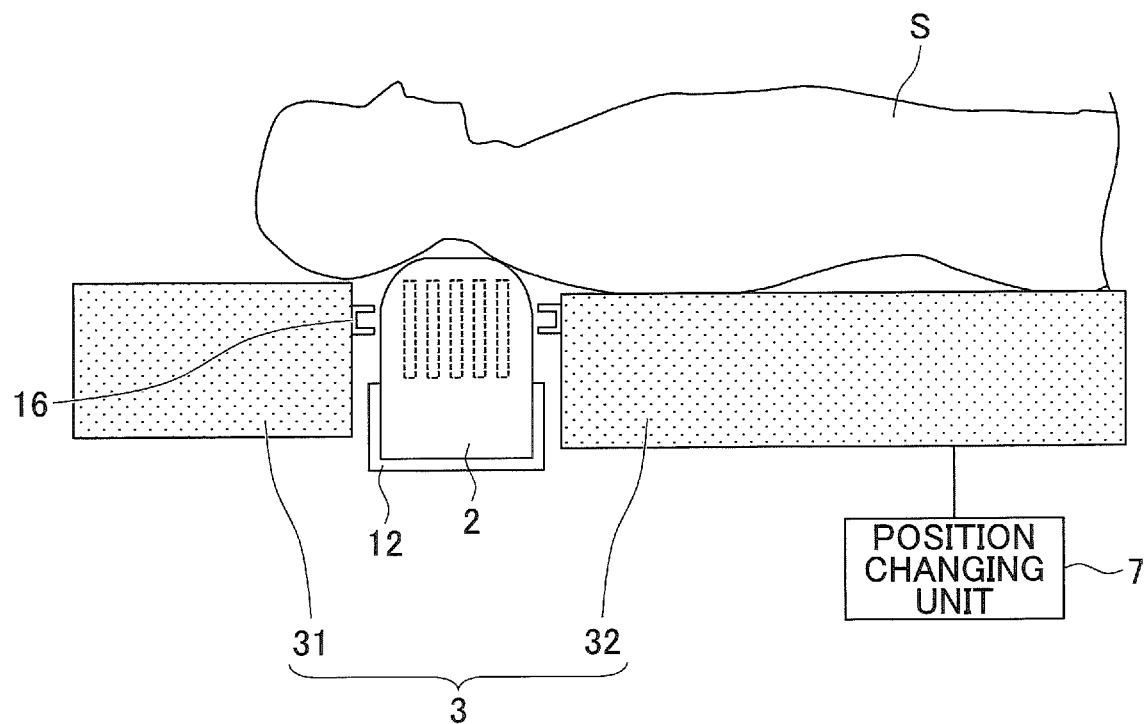
FIG. 17 is a view of a state in which a detachable bridge part is removed according to the first embodiment of the present invention.

In this method, radiation imaging is performed before the biomagnetic measurement; however, the biomagnetic measurement may be performed before radiation imaging. However, when the bridge part 4 is attachable to and detachable from the table 3, it is possible to perform biomagnetic measurement by removing the bridge part 4 as illustrated in FIG. 17, after radiation imaging. By removing the bridge part 4, the distance between the measurement region T and the magnetic sensors 21 of the biomagnetic detecting unit 2 can be shortened, so that the observed magnetic field signal becomes large and the precision of the biomagnetic measurement can be expected to be enhanced. Considering that the precision of the biomagnetic measurement improves by removing the bridge part 4 as described above, it is preferable to perform radiation imaging before biomagnetic measurement.

<Biomagnetic Measurement Method using Biomagnetic Measurement Apparatus 200>

Next, a biomagnetic measurement method using the biomagnetic measurement apparatus 200 will be described.

Figure 18:
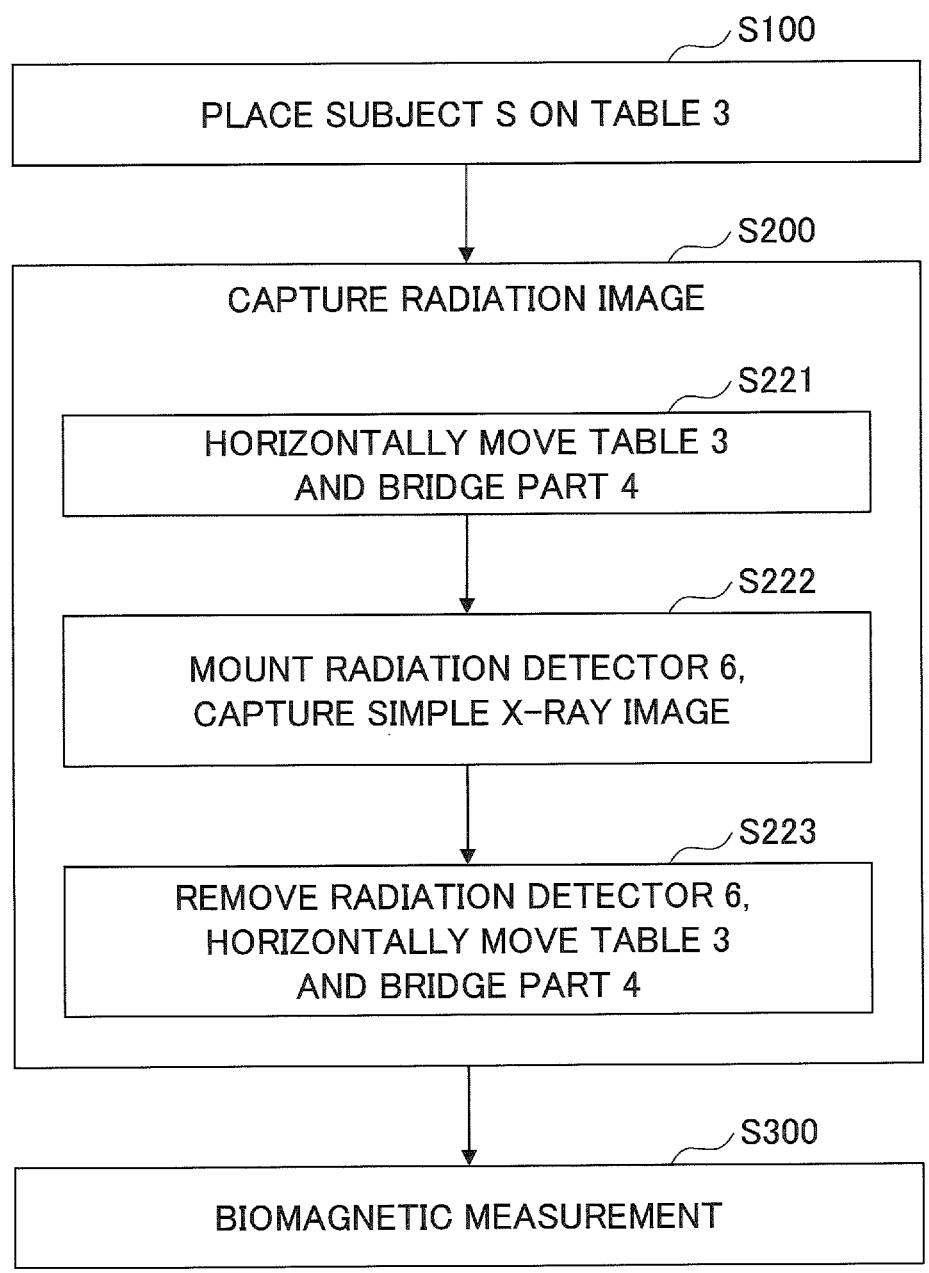
FIG. 18 is a flowchart illustrating a biomagnetic measurement method using the biomagnetic measurement apparatus according to the second embodiment of the present invention.

FIG. 18 is a flowchart illustrating a biomagnetic measurement method using the biomagnetic measurement apparatus 200. In the biomagnetic measuring method using the biomagnetic measurement apparatus 200, the content of radiation imaging is different from that of the biomagnetic measuring method using the biomagnetic measurement apparatus 100. That is, when radiation imaging is performed (step S200), first, the examiner operates the position changing unit 207 to synchronously move the table 3 and the bridge part 4 in the horizontal direction while the subject S is placed on the table 3 and the bridge part 4 (step S221). Subsequently, the examiner inserts the radiation detector 6 into the mounting part 16 in the space below the bridge part 4 formed as the bridge part 4 has moved from the position above the biomagnetic detecting unit 2, radiation is irradiated from the irradiation device 5 toward the subject S, and a simple x-ray image of the subject S is captured by the radiation detector 6 (step S222). Subsequently, the radiation detector 6 is removed from the mounting part 16, and the position changing unit 207 is operated to synchronously move the table 3 and the bridge part 4 in the horizontal direction to the original position (step S223). The other processes are the same as the biomagnetic measurement method using the biomagnetic measurement apparatus 100.

In this method as well, radiation imaging is performed before biomagnetic measurement; however, the biomagnetic measurement may be performed before radiation imaging. However, in consideration that the precision of the biomagnetic measurement is improved by removing the bridge part 4, it is preferable to perform radiation imaging before biomagnetic measurement.

<Biomagnetic Measurement Method using Biomagnetic Measurement Apparatus 300>

Figure 19:
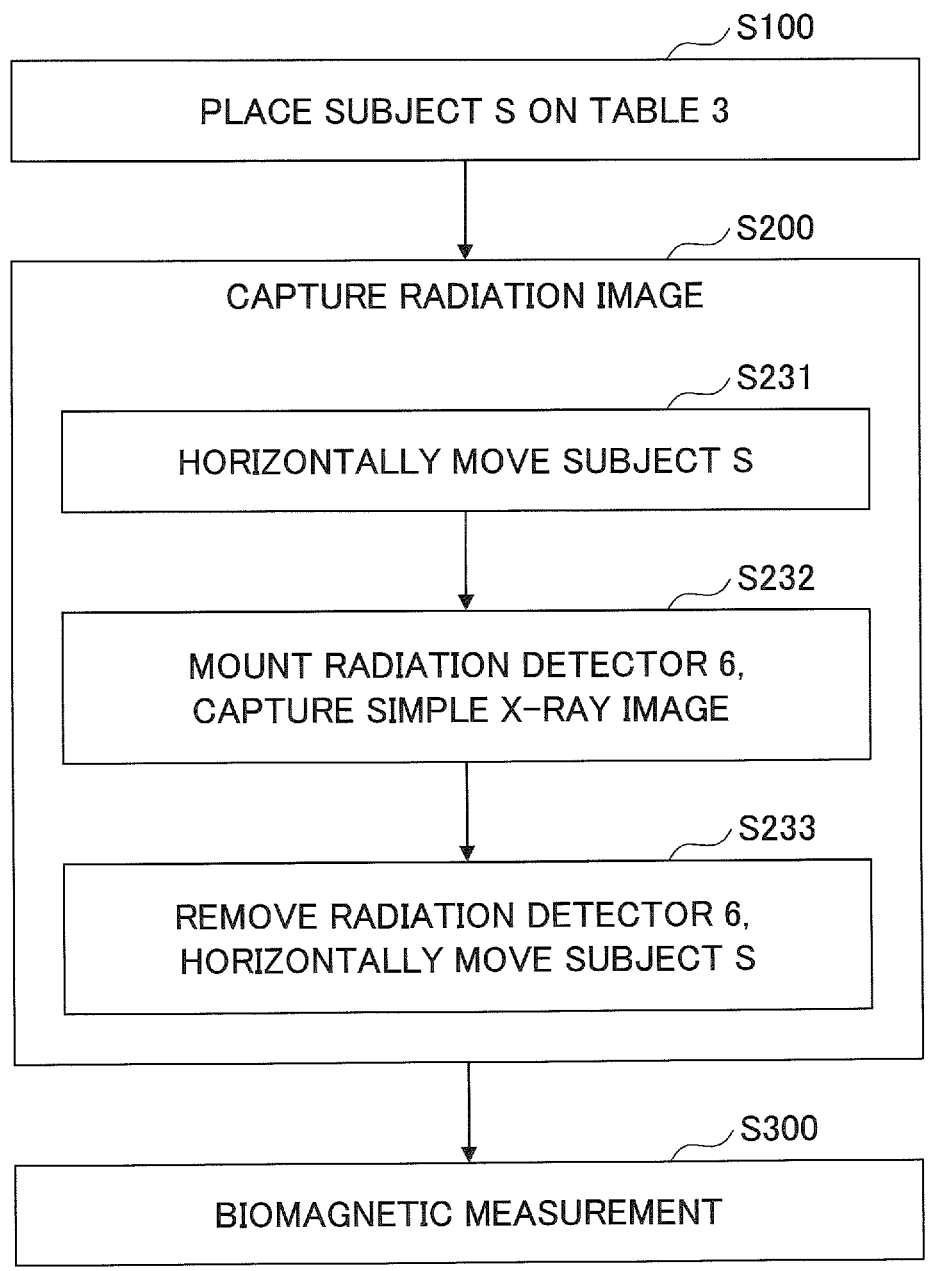
FIG. 19 is a flowchart illustrating a biomagnetic measurement method using the biomagnetic measurement apparatus according to the third embodiment of the present invention.

Next, a biomagnetic measurement method using the biomagnetic measurement apparatus 300 will be described. FIG. 19 is a flowchart illustrating a biomagnetic measurement method using the biomagnetic measurement apparatus 300. In the biomagnetic measuring method using the biomagnetic measurement apparatus 300, the content of radiation imaging is different from that of the biomagnetic measuring method using the biomagnetic measurement apparatus 100 or 200. That is, when radiation imaging is performed (step S200), first, the examiner operates the position changing unit 307 to move the subject S in the horizontal direction (step S231). At this time, the measurement region T is supported by the bridge part 4. Subsequently, the examiner inserts the radiation detector 6 into the mounting part 16 in the space below the bridge part 4, radiation is irradiated from the radiation irradiation device 5 toward the subject S, and a simple x-ray image of the subject S is captured by the radiation detector 6 (step S232). Subsequently, the radiation detector 6 is removed from the mounting part 16, and the position changing unit 307 is operated to move the subject S in the horizontal direction to the original position (step S233). The other processes are the same as the biomagnetic measurement method using the biomagnetic measurement apparatus 100.

In this method as'well, radiation imaging is performed before the biomagnetic measurement; however, the biomagnetic measurement may be performed before radiation imaging. Furthermore, in the biomagnetic measurement apparatus 300, the bridge part 4 is disposed so as to be deviated from the position directly above the biomagnetic detecting unit 2, and therefore biomagnetic measurement can be performed with high precision without removing the bridge part 4.

The measurement region T of the subject S is not limited to the spinal cord or the chest region, etc., and may be other regions or organs such as the brain, etc. It is preferable that the leading end surface 22a of the biomagnetic detecting unit 2 is shaped so as to be in close contact with the body surface of the measurement region T, and the bridge part 4 has a surface shape that corresponds to the leading end surface 22a.

According to one embodiment of the present invention, the image diagnosis result and the biomagnetic measurement result can be easily superimposed with high precision.

The biomagnetic measurement apparatus, the biological information measurement apparatus, and the biomagnetic measurement method are not limited to the specific embodiments described in the detailed description, and variations and modifications may be made without departing from the spirit and scope of the present invention.

What is claimed is:

1. A biomagnetic measurement apparatus comprising:
   a table on which a subject is placed;
   a biomagnetic detector configured to detect, a biomagnetic field of the subject;
   a supporter attached to the table and configured to support a detection target region from which the biomagnetic field of the subject is detected;
   a radiation detector holder configured to detachably hold a radiation detector and provided below the supporter; and
   a position changer configured to change relative positions of the biomagnetic detector and the detection target region, wherein
   the supporter has a surface shape that corresponds to a surface of the biomagnetic detector so as to contact with the biomagnetic detector in a position that the biomagnetic detector is in a closest position to the detection target region while the radiation detector is detached from the radiation detector holder.

2. The biomagnetic measurement apparatus according to claim 1, wherein the position changer moves the subject and the table, while a position of the biomagnetic detector is fixed.

3. The biomagnetic measurement apparatus according to claim 1, wherein the position changer moves the subject and the supporter, while a position of the biomagnetic detector is fixed.

4. lie biomagnetic measurement apparatus according to claim 1, wherein
   the position changer moves the subject, the table, and the supporter in a vertically upward direction, and
   the radiation detector is disposed in a gap that is formed between the biomagnetic detector and the supporter in a state that the position changer moves the subject and the supporter to an elevated position.

5. The biomagnetic measurement apparatus according to claim 1, wherein the position changer moves the subject in a horizontal direction, while a position of the biomagnetic detector is fixed.

6. The biomagnetic measurement apparatus according to claim 1, wherein the table includes a plurality of region-specific tables.

7. The biomagnetic measurement apparatus according to claim 6, wherein the supporter is disposed between the plurality of region-specific tables.

8. The biomagnetic measurement apparatus according to claim wherein the supporter is held so as to be detachable from the table.

9. A biomagnetic measurement apparatus configured to detect a biomagnetic field and capture a radiation image of a detection target region of a subject, comprises:
   a table on which a subject is placed;
   a biomagnetic detector configured to detect, a biomagnetic field of the subject;
   a supporter attached to the table and configured to support a detection target region from which the biomagnetic field of the subject is detected;
   a radiation detector holder configured to detachably hold a radiation detector and provided below the supporter; and
   a position changer configured to change relative positions of the biomagnetic detector and the detection target region,
   wherein the supporter has a surface shape that corresponds to a surface of the biomagnetic detector so as to contact with the biomagnetic detector in a position that the biomagnetic detector is in a closest position to the detection target region while the radiation detector is detached from the radiation detector holder, and
   wherein the biomagnetic detector and the radiation detector are configured to perform the detecting of the biomagnetic field and the capturing of the radiation image upon moving the subject to different positions respectively corresponding to the detecting of the biomagnetic field and the capturing of the radiation image, while maintaining a posture of the subject.

10. A biological information measurement apparatus comprising:
   a table on which a subject is placed;
   a first biological information detector configured to detect first biological information of the subject;
   a supporter attached to the table and configured to support a detection target region from which the first biological information of the subject is detected;
   a second biological information detector holder configured to detachably hold a second biological information detector configured to detect second biological information of the subject that is different from the first biological information, the second biological information detector being provided below the, supporter; and
   a position changer configured to change relative positions of the first biological information detector and the detection target region, wherein the supporter has a surface shape that corresponds to a surface of the first biological information detector so as to contact with the first biomagnetic detector in a position that the biomagnetic detector is in a closest position to the detection target region while the radiation detector is detached from the radiation detector holder.

11. The biological information measurement apparatus according to claim 10, wherein the first biological information does not include information relating to morphology of the subject, and
the second biological information includes a morphological image of the subject.

12. A biomagnetic measurement method comprising:
   placing a detection target region of a subject on a table so that the detection target region faces a supporter attached to the table;
   capturing a radiation image of a detection target region of the subject, by using a radiation detector;
   detecting a biomagnetic field of the detection target region, by using a biomagnetic detector; and
   changing relative positions of the biomagnetic detector and the detection target region, while maintaining a posture of the subject so that the detection target region faces the supporter, between the capturing of the radiation image and the detecting of the biomagnetic field, the supporter having a surface shape that corresponds to a surface of a biomagnetic detector so as to contact with the biomagnetic detector in a position that the biomagnetic detector is in a closest position to the detection target region while the radiation detector is detached from the radiation detector holder.

13. The biomagnetic measurement method according to claim 12, further comprising:
   removing the radiation detector from between the detection target region and the biomagnetic detector, before the detecting of the biomagnetic field.

14. The biomagnetic measurement method according to claim 12, wherein the capturing of the radiation image is performed while keeping the subject on a table and supporting the detection target region with a supporter having a surface shape that corresponds to a surface of the biomagnetic detector.

15. The biomagnetic measurement method according to claim 14, further comprising:
   removing the supporter from between the detection target region and the biomagnetic detector, before the detecting of the biomagnetic field.

16. The biomagnetic measurement apparatus according to claim 2, wherein the position changer simultaneously moves the supporter and the table.

17. The biomagnetic measurement apparatus according to claim 1, wherein the supporter includes an, electromagnetic coil embedded therein that is detected by the radiation detector and the biomagnetic detector.

18. The biomagnetic measurement apparatus according to claim 1, wherein the radiation detector holder has a cutout and the biomagnetic detector penetrates the radiation detector holder through the cutout when the biomagnetic detector is in the closest position to the detection target region while the radiation detector is detached from the radiation detector holder.

* * * * *